(12) United States Patent
Swenson

(10) Patent No.: US 8,614,236 B2
(45) Date of Patent: Dec. 24, 2013

(54) METHODS OF TREATING PULMONARY DISEASE USING ACETAZOLAMIDE AND STRUCTURALLY RELATED DERIVATIVES

(75) Inventor: Erik R. Swenson, Mercer Island, WA (US)

(73) Assignee: University of Washington, Seattle, WA (US)

( * ) Notice: Subject to any disclaimer, the term of this patent is extended or adjusted under 35 U.S.C. 154(b) by 790 days.

(21) Appl. No.: 11/953,249

(22) Filed: Dec. 10, 2007

(65) Prior Publication Data

US 2009/0131490 A1 May 21, 2009

Related U.S. Application Data

(60) Provisional application No. 60/869,635, filed on Dec. 12, 2006.

(51) Int. Cl.
*A61K 31/433* (2006.01)
(52) U.S. Cl.
USPC ........................................................ 514/363
(58) Field of Classification Search
None
See application file for complete search history.

(56) References Cited

U.S. PATENT DOCUMENTS

| | | | |
|---|---|---|---|
| 5,538,991 A | 7/1996 | Ashton et al. | |
| 2005/0090553 A1 | 4/2005 | Shapiro | |
| 2008/0226736 A1 * | 9/2008 | Caponetti et al. | 424/489 |

FOREIGN PATENT DOCUMENTS

| | | | |
|---|---|---|---|
| EP | 0 617 001 B1 | 1/2000 | |
| EP | 1 336 602 A1 | 8/2003 | |
| WO | 94/21590 A1 | 9/1994 | |
| WO | 95/31194 A1 | 11/1995 | |
| WO | 96/08486 A1 | 3/1996 | |
| WO | 96/08487 A1 | 3/1996 | |

OTHER PUBLICATIONS

Duffel et al. J. Med. Chem. 1986, vol. 29, 1488-1494.*
Hammond et al. Arch. Opthamol, vol. 116, Nov. 1998.*
"treatment." (2009). In Mosby's Dictionary of Medicine, Nursing, & Health Professions. Retrieved from <http://www.credoreference.com/entry/ehsmosbymed/treatment> on Nov. 18, 2010.*
Adis, "Acetazolamide: Best Prophylaxis of Acute Mountain Sickness When Slow Ascent Is Not Possible," Drugs Ther. Persp. 7(6):11-13 (1996).
Aslam & Khan, "The Role of Drugs in High Altitude Disorders," J. Pak. Med. Assoc. 46(4):90-92 (1996).
Berg et al., "Carbonic Anhydrase in Mammalian Vascular Smooth Muscle," J. Histochem. Cytochem. 52(8):1101-06 (2004).
Berg et al., "Inhibitors of Hypoxic Pulmonary Vasoconstriction Prevent High-altitude Pulmonary Edema in Rats," Wilderness Environ. Med. 15:32-37 (2004).
Bradwell et al., "Acetazolamide and High Altitude Diseases," Int'l J. Sports Med. 13:S63-S64 (1992).
Deem et al., "Acetazolamide Reduces Hypoxic Pulmonary Vasoconstriction in Isolated Perfused Rabbit Lungs," Resp. Physiol. 123:109-19 (2000).
Gislason et al., "Exudative Retinal Detachment in Familial Pulmonary Hypertension," Acta Ophthalmologica 69:805-09 (1991).
Pickkers et al., "Inhibition of Carbonic Anhydrase Accounts for the Direct Vascular Effects of Hydrochlorothiazide," Hypertension 33:1043-1048 (1999).
Höhne et al., "Acetazolamide Prevents Hypoxic Pulmonary Vasoconstriction in Conscious Dogs," J. Appl. Physiol, 97:515-21 (2004).
Höhne at al., Abstract A716, "Acetazolamide Does Not Prevent Hypoxic Pulmonary Vasoconstriction by Carbonic Anhydrase Inhibition," American Thoracic Society International Meeting (May 2006).
Höhne et al., Poster A77, "Acetazolamide Does Not Prevent Hypoxic Pulmonary Vasoconstriction by Carbonic Anhydrase Inhibition," American Thoracic Society International Meeting, presented May 23, 2006.
Hussain & Aslam, "Hypoxia and Pulmonary Acclimatisation at 4578 M Altitude: The Role of Acetazolamide and Dexamethasone," J. Pak. Med. Assoc. 53(10):451-58 (2003).
Jen et al., "Spinocerebellar Ataxia Type 6 with Positional Vertigo and Acetazolamide Responsive Episodic Ataxia," J. Neurol. Neurosurg. Psychiatry 65:565-68 (1998).

(Continued)

*Primary Examiner* — Alicia L Otton
(74) *Attorney, Agent, or Firm* — Mark J. FitzGerald; Nixon Peabody LLP

(57) ABSTRACT

The present invention is directed to a method of treating a subject for a pulmonary disease by administering a therapeutically effective amount of a compound of the formula:

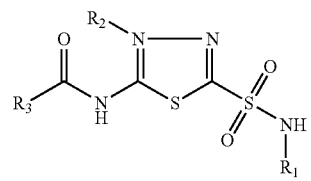

wherein $R_1$, $R_2$ or $R_3$ are each independently a $C_1$ to $C_6$ alkyl, a halogen, a sulfate, or a phosphate. The pulmonary disease in the subject can be hypoxic pulmonary vasoconstriction, pulmonary edema, pulmonary hypertension, asthma, chronic obstructive pulmonary disease, cystic fibrosis, interstitial fibrosis, high altitude residence, sleep apnea syndrome, atrial septal defects, and pulmonary diseases associated with other conditions. If this same compound is modified so that $R_1$, $R_2$ or $R_3$ each independently is a $C_1$ to $C_6$ alkyl and the compound is not a carbonic acid inhibitor, it can be administered to a subject to block hypoxic pulmonary vasoconstriction and/or prevent high altitude pulmonary edema. Additional aspects of the present invention include an inhalable composition comprising the compound of the above formula without modification and an inhalable carrier, as well as the above modified compound.

2 Claims, 11 Drawing Sheets

(56) References Cited

OTHER PUBLICATIONS

Kiwull-Schöne & Kiwull, "Hypoxia and the 'Reaction Theory' of Central Respiratory Chemosensitivity," in 316 Advances in Experimental Medicine and Biology: Oxygen Transport to Tissue XIII, 347-57 (Thomas K. Goldstick et al. eds., 1992).

Lehenkari et al., "Carbonic Anhydrase II Plays a Mayor Role in Osteoclast Differentiation and Bone Resorption by Effecting the Steady State Intracellular pH and Ca2+," Exp. Cell Res. 242:128-37 (1998).

Rodway et al., "High-altitude-related Disorders—Part I: Pathophysiology, Differential Diagnosls, and Treatment," Heart Lung 32(6):353-59 (2003).

Shimoda et al., Abstract 704.3, "Acetazolamide (AZ) Prevents Hypoxia-induced Increases in Intracellular Ca2+ Concentration ([Ca2+]i) in Rat Pulmonary Arterial Smooth Muscle Cells (PASMCs) by a Mechanism Independent of Carbonic Anhydrase (CA) Inhibition," Experimental Biology/IUPS 2005: Meeting Abstracts, at A1309 (2005).

Shimoda et al, Abstract A758, "Blockade of Hypoxia-induced Increases in Intracellular Ca2+ Concentration ([Ca2+]i) by Acetazolamide (AZ) in Pulmonary Arterial Smooth Muscle Cells (PASMCs) Is Independent of Carbonic Anhydrase (CA) Inhibition," American Thoracic Society International Meeting (May 2006).

Shlim, High Altitude Medical Advice for Travelers (1997), http://www.ciwec-clinic.com/articles/del_14-may-2009_high_altitude.php.

Swenson, "Carbonic Anhydrase Inhibitors and Hypoxic Pulmonary Vasoconstriction," Resp. Physiol. Neurobiol. 151:209-16 (2006).

Tojima et al., "Difference in the Effects of Acetazolamide and Ammonium Chloride Acidosis on Ventilatory Responses to CO2 and Hypoxia in Humans," Jap. J. Physiol, 36:511-521 (1986).

Tojima et al., "Effects of Acetazolamide on Pulmonary Function and Ventilatory Responses to Hypercapnia and Hypoxia in Healthy Male Subjects," Kokyu to Junkan 34:69-74 (1986).

Shimoda et al., "Blockade of Hypoxia-induced Increases in Intracellular Ca2+ Concentration ([Ca2+]i) by Acetazolamide (AZ) in Pulmonary Arterial Smooth Muscle Cells (PASMCs) Is Independent of Carbonic Anhydrase (CA) inhibition," Proceedings of the American Thoracic Society, Abstracts ATS 2006 International Conference, vol. 3 (Abstracts Issue) (Apr. 2006).

Shimoda et al., "Inhibition of Hypoxia-induced Calcium Responses in Pulmonary Arterial Smooth Muscle by Acetazolamide is Independent of Carbonic Anhydrase Inhibition," Am. J. Physiol. Lung Cell Mol. Physiol. 292:L1002-L1012 (2007).

Cox, S.N. et al., "Treatment of Chronic Macular Edema With Acetazolamide," Arch Ophthalmol. 106:190-1195 (1988).

Maren, T., "Carbonic anhydrase inhibition. V. N5-substituted 2-acetylamino-1,3,4-thiadiazole-5-sulfonamides: metabolic conversion and use as control substances," J. Pharmacol. Exp. Ther. 117(4):385-401 (1956).

\* cited by examiner

| | MW | $K_i$ vs CA II | pKa | ether partition coefficient | water solubility |
|---|---|---|---|---|---|
| Acetazolamide | 222 | 8 | 7.4 | 0.14 | 50 |
| N-methyl acetazolamide | 236 | 1600 | 7.7 | 0.15 | 45 |
| Ethoxzolamide | 258 | 1 | 8.1 | 140 | 4 |
| Benzolamide | 320 | 2 | 3.2 | 0.001 | 45 |

Figure 1

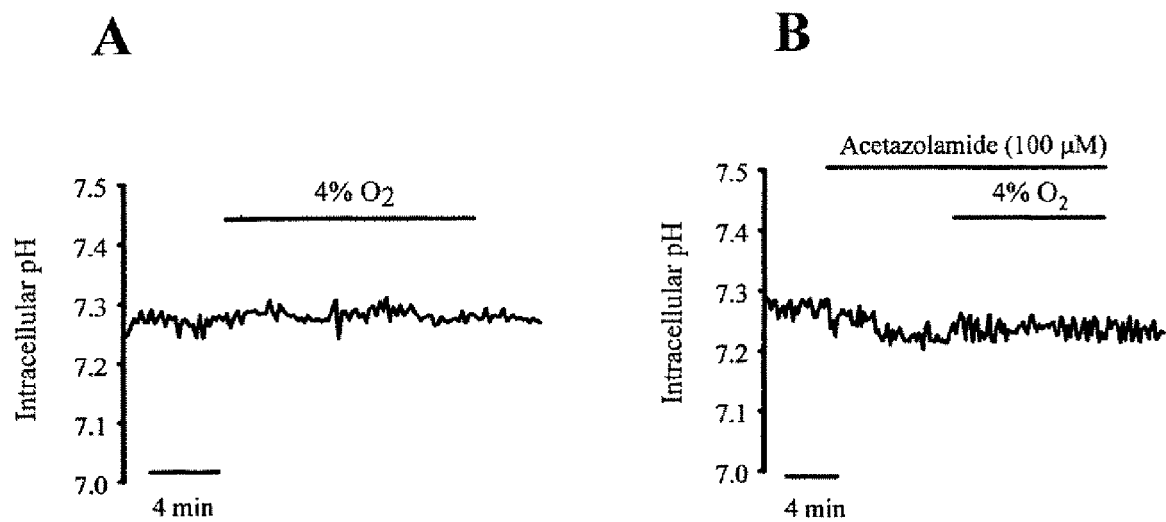
Figures 2A-B

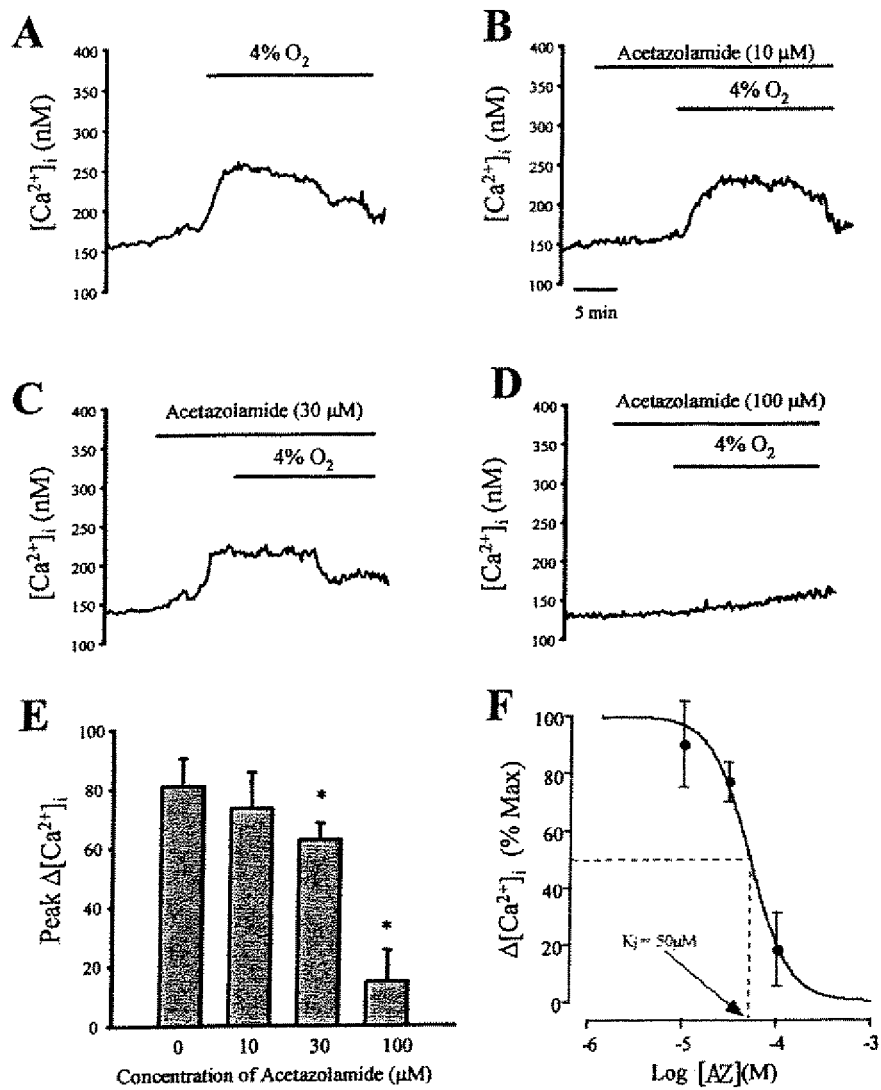
Figures 3A-F

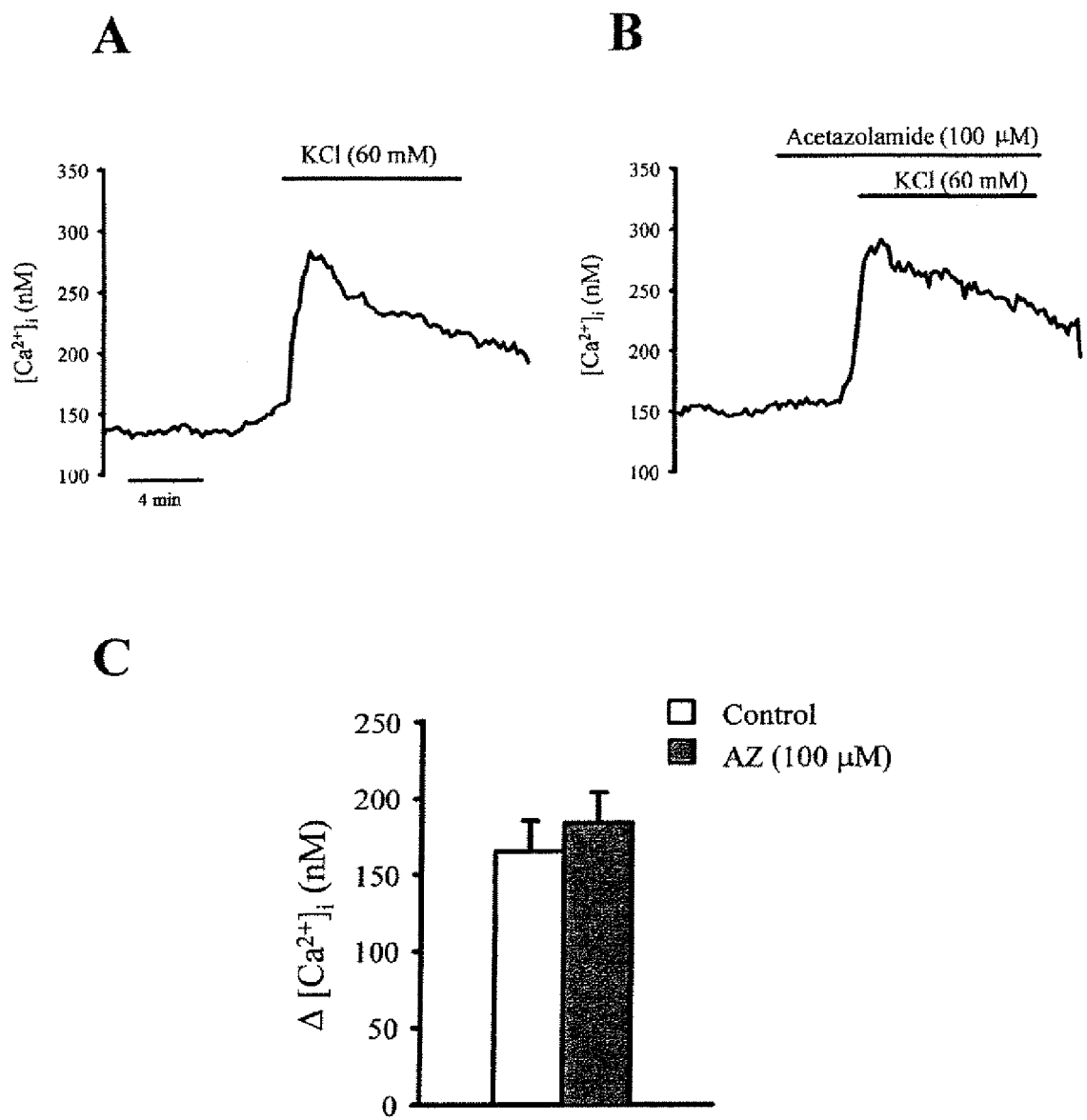
Figures 4A-C

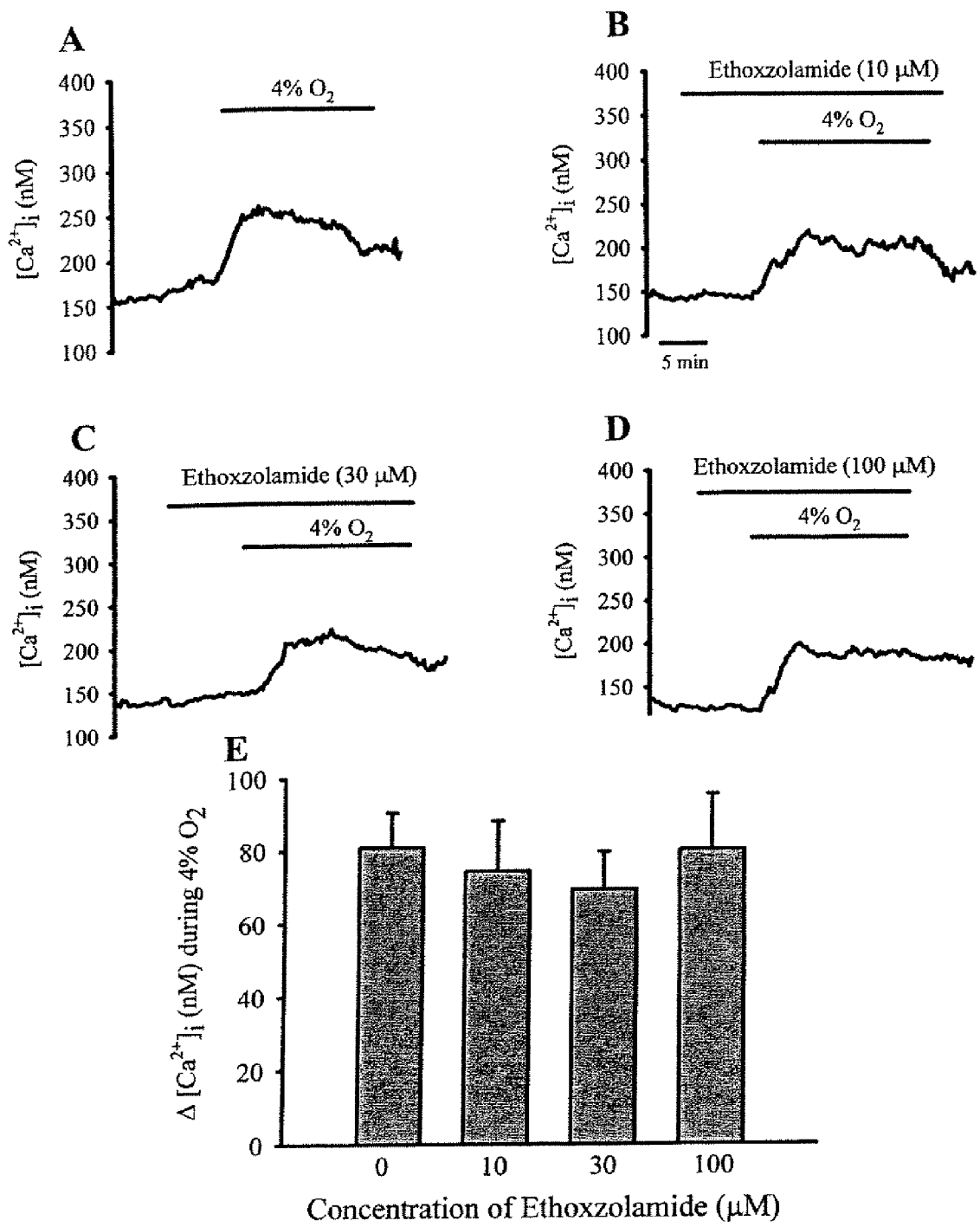
Figures 5A-E

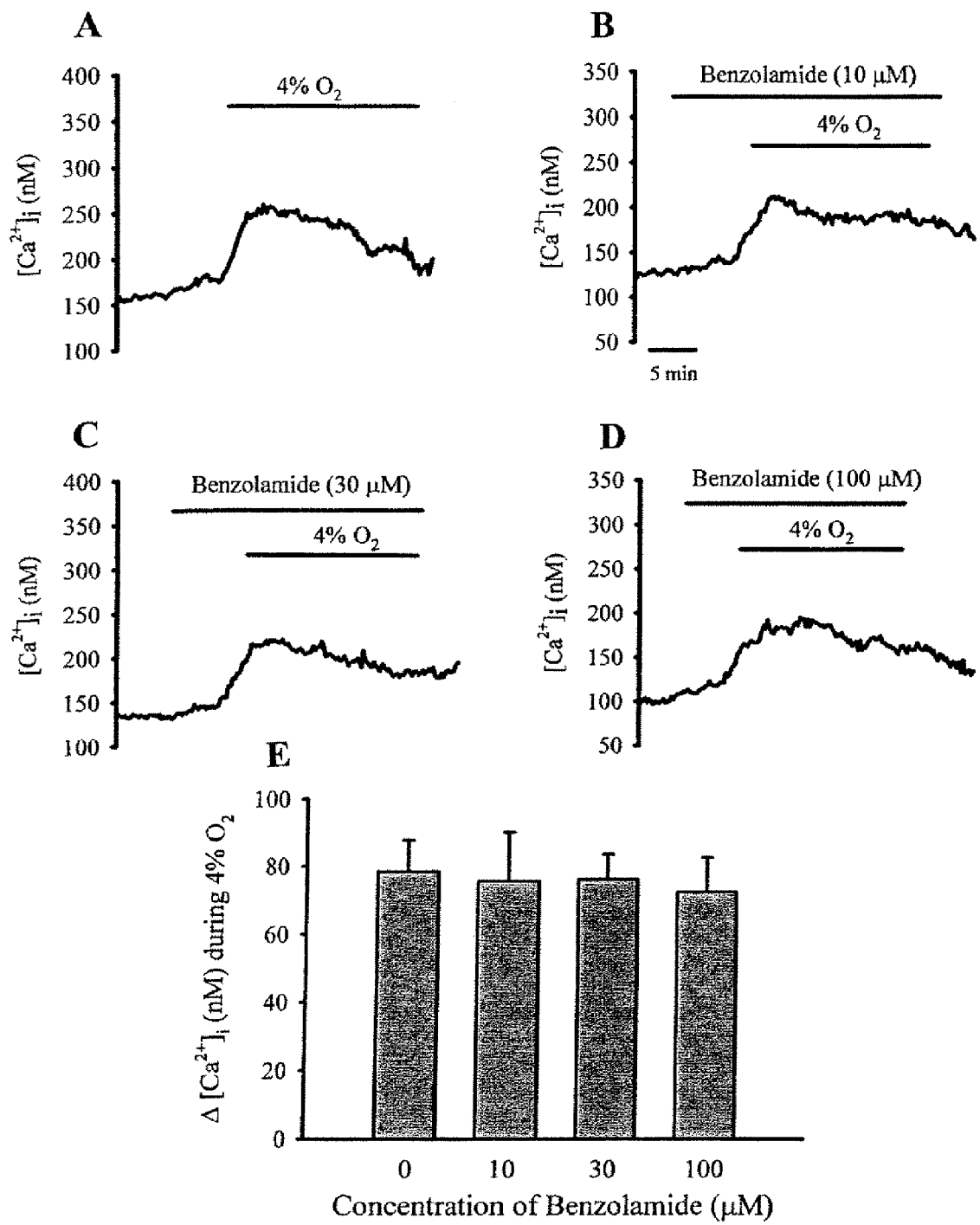
Figures 6A-E

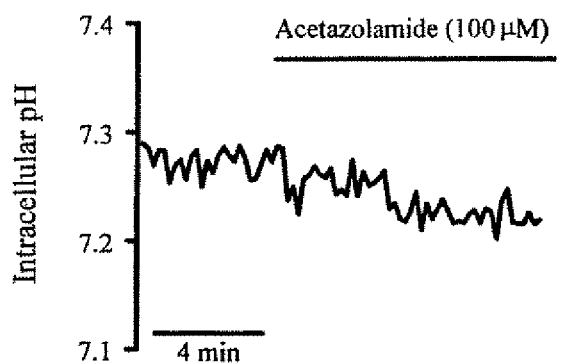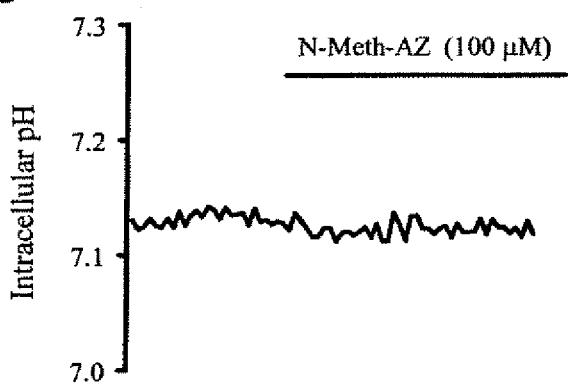
Figures 7A-B

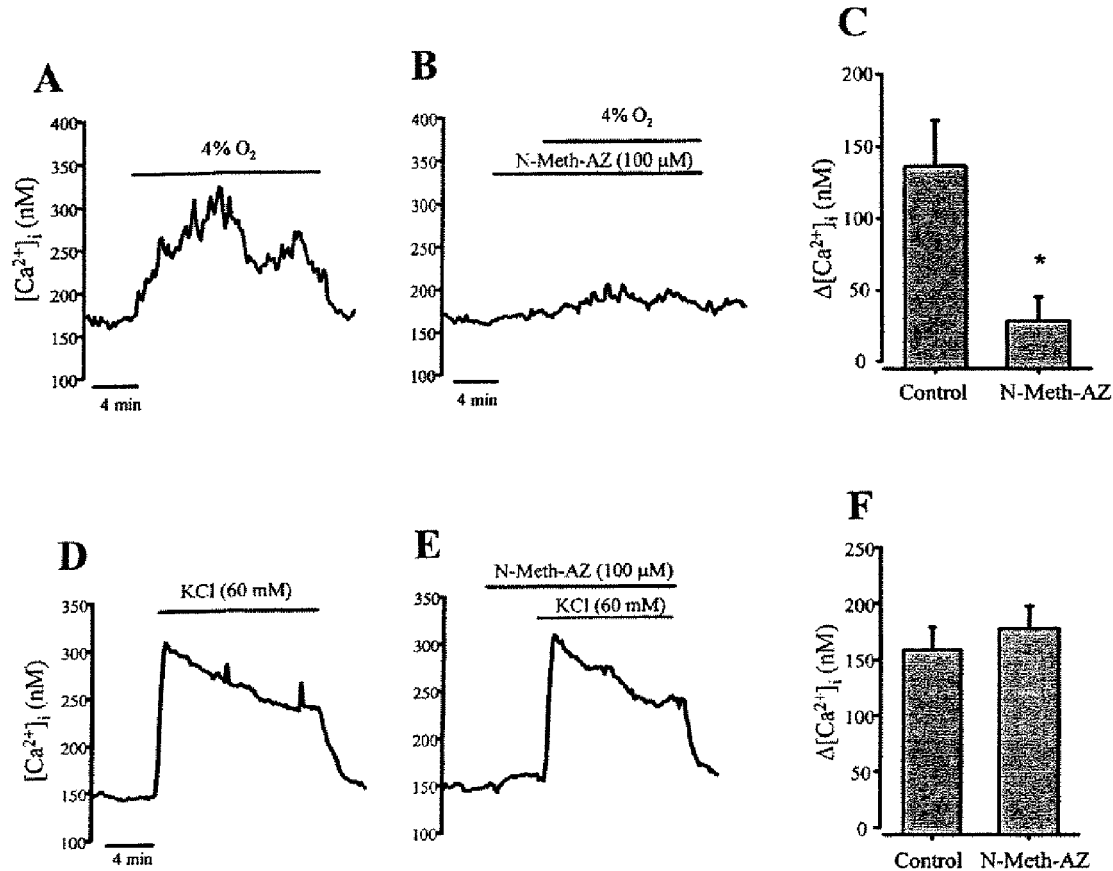
Figures 8A-F

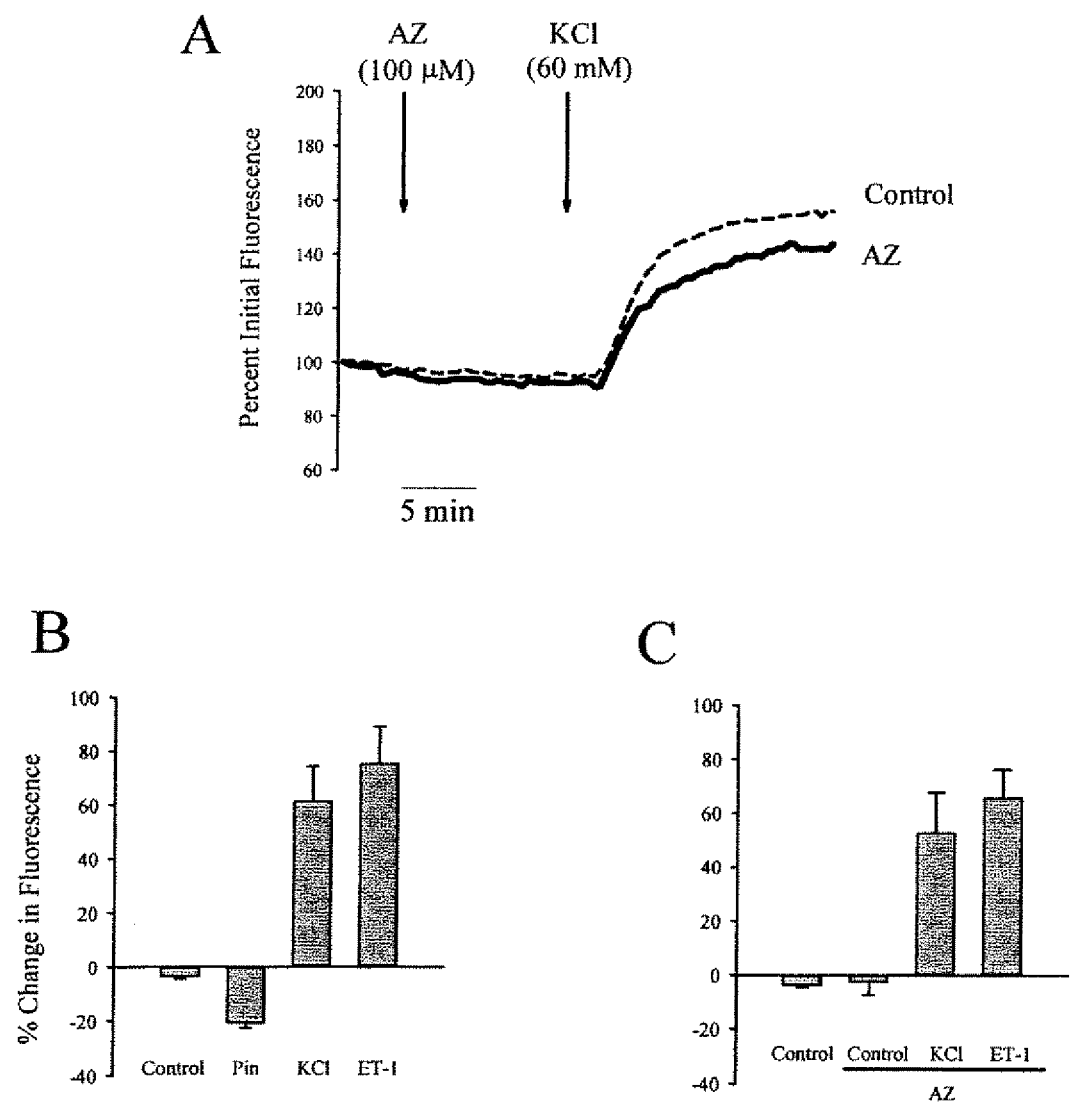
Figures 9A.-C

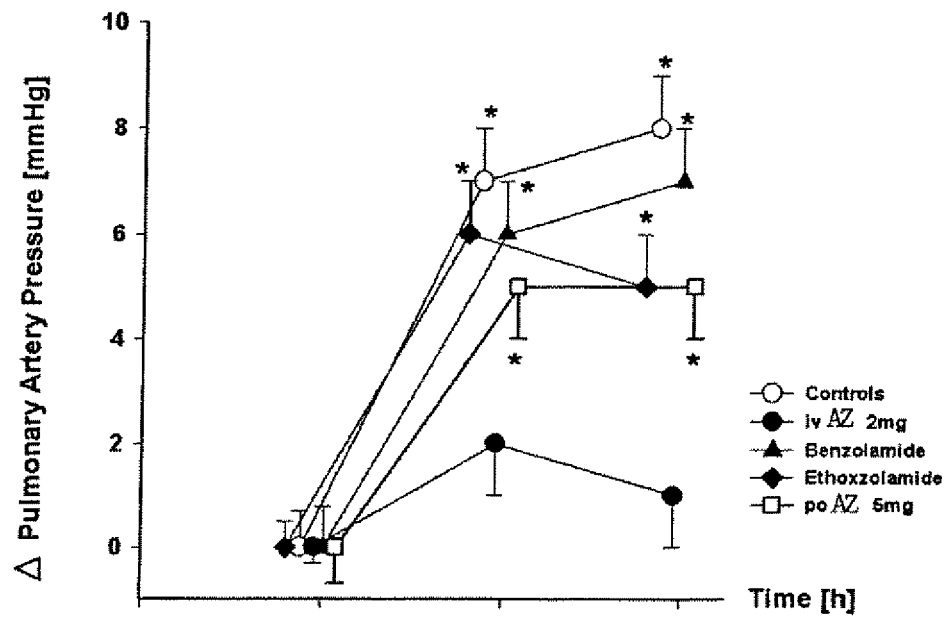
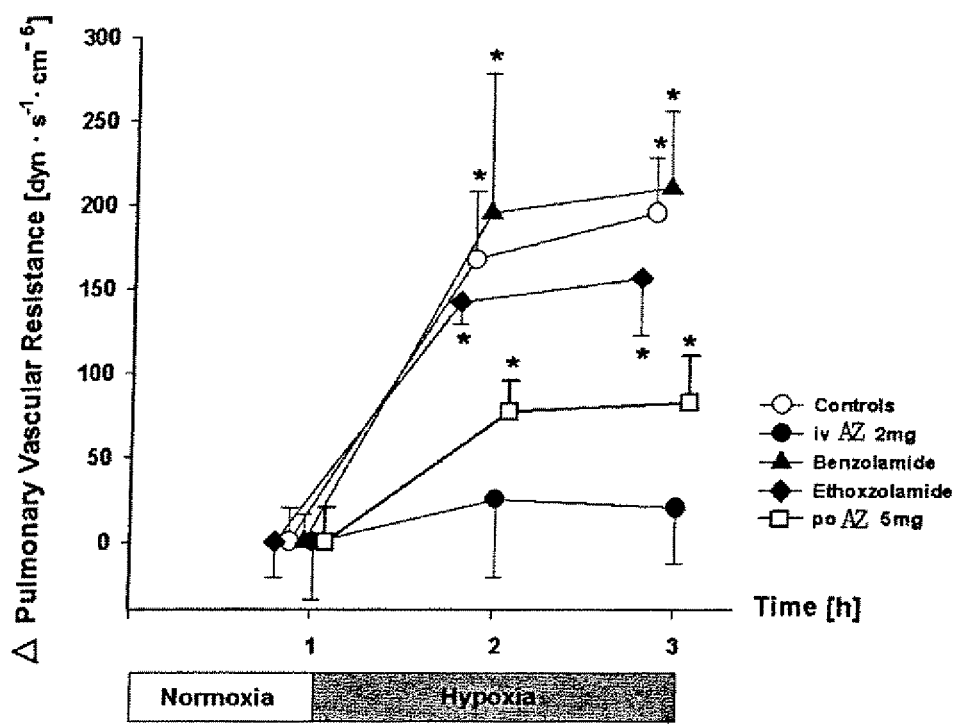
Figures 10A-B

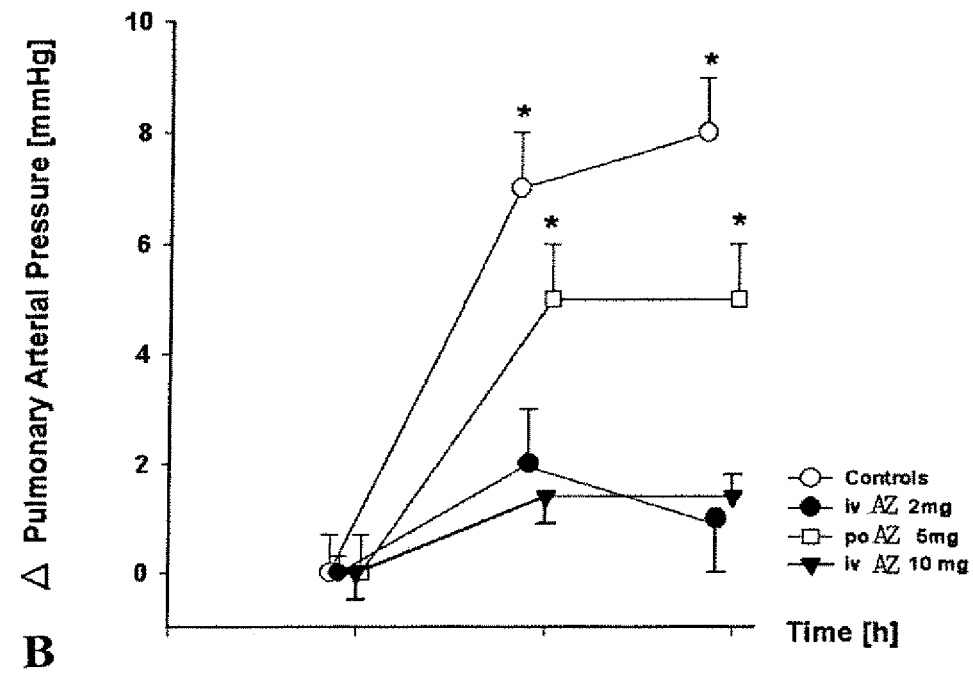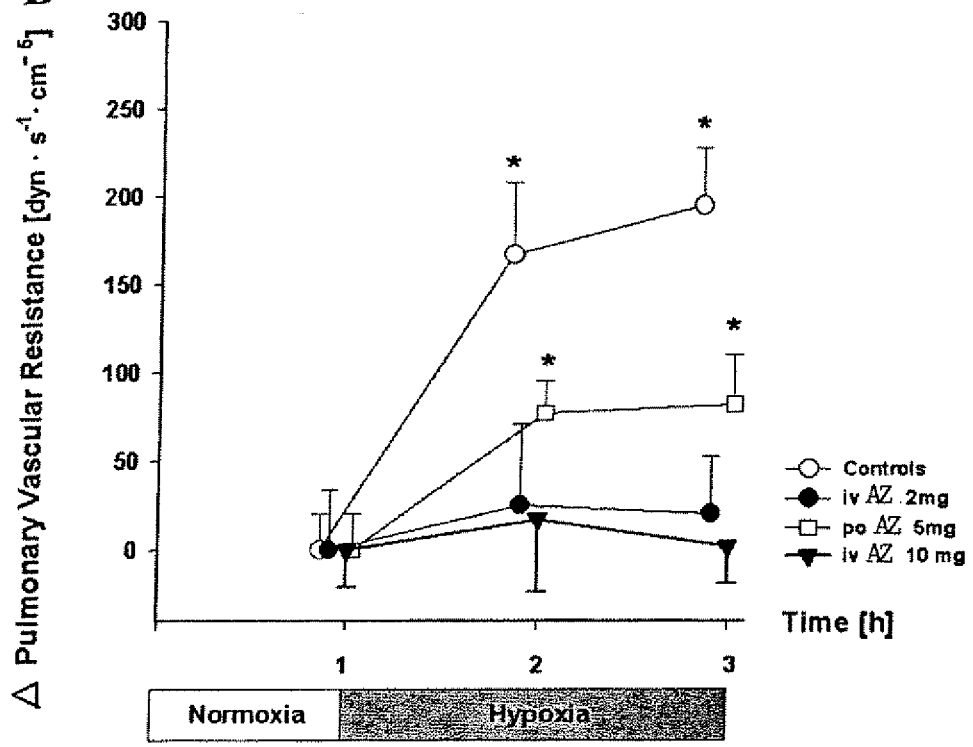
Figures 11A-B

METHODS OF TREATING PULMONARY DISEASE USING ACETAZOLAMIDE AND STRUCTURALLY RELATED DERIVATIVES

This application claims benefit of U.S. Provisional Patent Application Ser. No. 60/869,635, filed Dec. 12, 2006, which is hereby incorporated by reference in its entirety.

The present invention was made with government support under Grant No. HL-24163 awarded by the National Institutes of Health. The government has certain rights in this invention.

FIELD OF THE INVENTION

The present invention relates to methods of treating pulmonary disease using acetazolamide and structurally related derivatives.

BACKGROUND OF THE INVENTION

Alveolar hypoxia, as occurs with ascent to high altitude or chronic lung diseases, results in hypoxic pulmonary vasoconstriction (HPV). Exaggerated HPV causes high altitude pulmonary edema (HAPE) (Bartsch P, et al., *J Appl Physiol* 98: 1101-1110 (2005)) and may complicate the course of patients with chronic cardiopulmonary disease. Despite extensive study, the exact cellular mechanisms by which hypoxia induces HPV remain poorly understood. HPV is generally believed to require $Ca^{2+}$ influx into pulmonary arterial smooth muscle cells (PASMCs), as HPV is attenuated by removal of extracellular $Ca^{2+}$ and by antagonists of voltage-gated $Ca^{2+}$ channels (McMurtry I. F., et al., *Circ Res* 38: 99-104 (1976); Naeije R., et al., *Chest* 82: 404-410 (1982); Redding G. J., et al., *Am Rev Respir Dis* 129: 785-789 (1984); Simonneau G., et al., *N Engl J Med* 304: 1582-1585 (1981); Stanbrook H. S., et al., *Am Rev Respir Dis* 130: 81-85 (1984); Suggett A. J., et al., *Clin Exp Pharmacol Physiol* 7: 263-274 (1980); Tucker A., et al., *Proc Soc Exp Biol Med* 151: 611-614 (1976). HPV can also be modulated by changes in intracellular pH ($pH_i$) (Raffestin B., et al., *J Appl Physiol* 63: 2524-2531 (1987) and extracellular pH (Loeppky J. A., et al., *J Appl Physiol* 72: 1787-1797 (1992)).

The oral carbonic anhydrase (CA) inhibitor acetazolamide (AZ) is frequently used for prevention and treatment of acute mountain sickness (AMS) and to augment ventilation for high altitude acclimatization (Swenson E. R., et al., *Eur Respir J* 12:1242-1247 (1998); Swenson E. R., *Resp Physiol Neurobiol.* 151(2-3): 209-16 (2006)). When taken prior to ascent, AZ can prevent the development of acute mountain sickness by its effects on renal bicarbonate reabsorption and chemoreceptor activity to increase ventilation and increase arterial oxygenation. As a respiratory stimulant AZ raises alveolar $PO_2$ and might by this mechanism blunt HPV and prevent HAPE, as do other pulmonary vasodilators that reduce HPV, such as nifedipine (Bartsch P., et al., *N Engl J Med* 325: 1284-1289 (1991)). Work in intact animals and isolated perfused lung preparations, has demonstrated that AZ attenuates the magnitude of HPV and slows the onset of the response (Deem S., et al., *Respir Physiol* 123: 109-119 (2000); Emery C. J., et al., *Bull Eur Physiopathol Respir* 13: 763-776 (1977); Hohne C., et al., *J Appl Physiol* 97: 515-521 (2004)), although the cellular mechanism by which this occurs remains uncertain. Although in vivo AZ might blunt HPV additionally by its respiratory effect, a direct effect independent of ventilation-induced changes in alveolar $PO_2$ is evident since AZ inhibits HPV when ventilation, alveolar $PO_2$ and $PCO_2$ are carefully controlled or held constant (Deem S., et al., *Respir Physiol* 123: 109-119 (2000); Emery C. J., et al., *Bull Eur Physiopathol Respir* 13; 763-776 (1977); Hohne C., et al., *J Appl Physiol* 97:515-521 (2004)). Although originally developed as a diuretic with primary action on the kidney, vascular smooth muscle contains CA (Berg J. T., et al., *J Histochem Cytochem* 52: 1101-1106 (2004)) and AZ has been proposed to have direct effects on smooth muscle function in systemic blood vessels independent of its diuretic actions. The mechanisms involved in the vasodilatory effect of AZ on systemic vascular smooth muscle (Pickkers P., et al., *Br J Pharmacol* 132: 443-450 (2001)), which may include modulation of $K^+$ channels, membrane potential, $Ca^{2+}$ signaling or intracellular pH ($pH_i$), are just beginning to be explored. For example, in various cell types carbonic anhydrase inhibitors block $Ca^{2+}$ channels (Gottfried J. A. and Chesler M., *J Neurophysiol* 74: 2774-2777 (1995); Jahromi S. S., et al., *Brain Res* 872: 20-28 (2000); McNaughton N. C., et al., *J Pharmacol Sci* 95: 240-247 (2004); Zhang X., et al., *Epilepsia* 41 Suppl 1: S52-60 (2000)), inhibit a $Cl^-$-dependent ATPase (Chipperfield A. R., et al., *Biochem Biophys Res Commun* 194: 407-412 (1993)) and activate $Ca^{2+}$-activated $K^+$ channels (Pickkers P., et al., *Br J Pharmacol* 132: 443-450 (2001); Tricarico D., et al., *Ann Neurol* 48: 304-312 (2000); Tricarico D., et al., *Faseb J* 18: 760-761 (2004)). The effect of AZ and/or carbonic anhydrase inhibition on pulmonary artery smooth muscle cell (PASMC) function is unknown.

The present invention is directed toward overcoming these deficiencies in the art.

SUMMARY OF THE INVENTION

One aspect of the present invention is directed to a method of treating a subject for a pulmonary disease by administering a therapeutically effective amount of a compound of the formula:

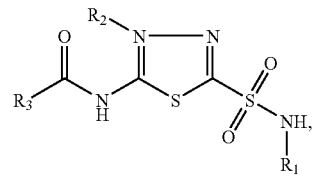

where $R_1$, $R_2$, and $R_3$ are each independently selected from the group consisting of hydrogen, a $C_1$ to $C_6$ alkyl, a halogen, a sulfate, and a phosphate. The pulmonary disease can be hypoxic pulmonary vasoconstriction, pulmonary edema, pulmonary hypertension, asthma, chronic obstructive pulmonary disease, cystic fibrosis, interstitial fibrosis, high altitude residence, sleep apnea syndrome, atrial septal defects, and pulmonary diseases associated with other conditions.

Another aspect of the present invention relates to a method of blocking hypoxic pulmonary vasoconstriction and/or preventing high altitude pulmonary edema in a subject. This is carried out by administering a compound which is not a carbonic acid inhibitor and has the formula:

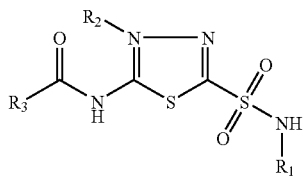

where $R_1$, $R_2$, and $R_3$ are each independently selected from the group consisting of hydrogen, a $C_1$ to $C_6$ alkyl, a halogen, a sulfate, or a phosphate. Such administration is carried out under conditions effective to block hypoxic pulmonary vasoconstriction and/or prevent high altitude pulmonary edema in the subject.

A further aspect of the present invention pertains to an inhalable composition comprising a compound of the formula:

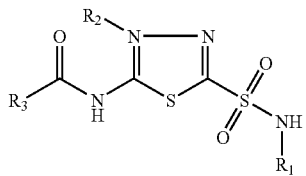

wherein $R_1$, $R_2$, and $R_3$ are each independently selected from the group consisting of hydrogen, a $C_1$ to $C_6$ alkyl, a halogen, a sulfate, or a phosphate, and an inhalable carrier for the compound.

The present invention is also directed to a compound which is not a carbonic acid inhibitor and has the formula:

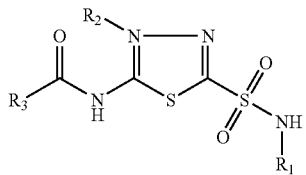

where $R_1$, $R_2$ and $R_3$ each independently are a $C_1$ to $C_6$ alkyl.

The expected benefits of the present invention include a new oral and inhaled medication for the treatment of pulmonary hypertension. Several forms of pulmonary hypertension are anticipated to be effectively treated including primary or idiopathic pulmonary hypertension, those forms secondary to chronic lung diseases (chronic obstructive pulmonary disease, interstitial fibrosis, cystic fibrosis), short and long term high altitude residence, sleep apnea syndrome, atrial septal defects with left to right shunting, and those associated with other conditions such as chronic liver disease, anorexigenic drugs, and human immunodeficiency virus (HIV) disease. This will be a drug of a new class and action, so it is expected that it may add further reduction to pulmonary artery pressure when combined with existing approved agents in an evolving strategy of multiple drug treatment of pulmonary hypertension. Any drugs of this class with a change in the structure of acetazolamide that eliminate its carbonic anhydrase inhibiting activity will have the added benefit of being free of the side effects that develop with chronic carbonic anhydrase inhibition.

BRIEF DESCRIPTION OF THE DRAWINGS

FIG. 1 shows the structures and properties of the CA inhibiting and non-inhibiting sulfonamides.

FIGS. 2A-B show composite traces, demonstrating the effect of hypoxia on $pH_i$ in the absence (FIG. 2B) and presence of AZ (100 μM) (FIG. 2A). While AZ caused a small decrease in $pH_i$, hypoxia had no effect on $pH_i$ in either control cells (n=85 cells) or cells treated with AZ (n=55 cells).

FIGS. 3A-D show composite traces, illustrating the effect of hypoxia on $[Ca^{2+}]_i$ in the absence (n=115 cells) (FIG. 3A) and presence of AZ (10, 30, and 100 μM) (FIGS. 3B-D, respectively). In the absence of AZ, hypoxia caused a rapid, reversible increase in $[Ca^{2+}]_i$. AZ caused a dose-dependent inhibition of the hypoxia-induced $Ca^{2+}$ response, with almost complete blockade at 100 μM (n=73 cells).

FIG. 3E is a bar graph representing the effect of AZ on the peak change in $[Ca^{2+}]_i$ induced by hypoxia (n=38 cells for 10 μM; n=60 cells for 30 μM). The symbol * indicates significant difference from control value (p<0.05).

FIG. 3F shows a concentration response plot, demonstrating $IC_{50}$ of AZ.

FIGS. 4A-B show composite traces, illustrating the effect of AZ (100 μM) on KCl-induced increases in $[Ca^{2+}]_i$. In the absence of AZ, KCl (60 mM) induced a rapid increase in $[Ca^{2+}]_i$ (n=40 cells) (FIG. 4A). Addition of AZ had no effect on the KCl-induced increase in $[Ca^{2+}]_i$ (n=43 cells) (FIG. 4B).

FIG. 4C shows a bar graph, representing mean change in $[Ca^{2+}]_i$ induced by KCl in the absence and presence of AZ.

FIGS. 5A-D show composite traces, illustrating the effect of ethoxzolamide (EZ; 10, 30, and 100 μM), a CA inhibitor with high membrane permeability, on hypoxia-induced increases in $[Ca^{2+}]_i$.

FIG. 5E is a bar graph representing average peak change in $[Ca^{2+}]_i$ in response to hypoxia in the absence (n=115 cells) and presence of EZ (n=60 cells for 10 μM; n=68 cells for 30 μM; n=88 cells for 100 μM). EZ had no effect on the peak change in $[Ca^{2+}]_i$ induced by hypoxia at any of the concentrations tested.

FIGS. 6A-D show composite traces, illustrating the effect of benzolamide (BZ; 10, 30, and 100 μM), a CA inhibitor with poor membrane permeability, on hypoxia-induced increases in $[Ca^{2+}]_i$.

FIG. 6E is a bar graph representing average peak change in $[Ca^{2+}]_i$ in response to hypoxia in the absence (n=115 cells) and presence of BZ (n=65 cells for 10 μM; n=125 cells for 30 μM; n=50 cells for 100 μM). BZ had no effect on the peak change in $[Ca^{2+}]_i$ induced by hypoxia at any of the concentrations tested.

FIGS. 7A-B show composite traces, demonstrating the effect of 100 μM AZ (FIG. 7A) and N-Meth-AZ (FIG. 7B) on intracellular pH ($pH_i$) in PASMCs. AZ caused a small decrease in $pH_i$ (n=55 cells) while N-Meth-AZ (n=81 cells) had no significant effect on $pH_i$.

FIGS. 8A-F show composite traces and bar graphs, demonstrating the effect of (A) hypoxia (4% $O_2$) (FIGS. 8A-C) and (B) 60 mM KCl (FIGS. 8D-F) on $[Ca^{2+}]_i$ in the absence and presence of 100 μM N-Meth-AZ. Hypoxia caused a significant increase in $[Ca^{2+}]_i$ in control cells (n=78 cells), but had no effect on $[Ca^{2+}]_i$ in the presence of N-Meth-AZ (n=63 cells). In contrast, $[Ca^{2+}]_i$ increased to a similar extent in response to KCl in the absence (n=83 cells) and presence (n=73 cells) of N-Meth-AZ.

FIG. 9A shows composite traces, demonstrating effect of KCl (80 mM) and AZ (100 μM) on DiBAC4(3) (490 nm) fluorescence.

FIG. 9B is a bar graph showing mean change in fluorescence in untreated cells (control; n=90) and cells exposed to the hyperpolarizing agent, pinacidil (100 μM; n=58) or the depolarizing agent, KCl (n=109).

FIG. 9C is a bar graph showing mean change in fluorescence in basal fluorescence and in response to KCl in the absence (n=109) and presence (n=90) of AZ.

FIGS. 10A-B are graphs showing differences between values obtained during normoxia and the first and second hour of hypoxia in controls, iv AZ, po AZ, benzolamide, and ethoxzolamide for mean pulmonary artery pressure and for pulmonary vascular resistance. Values are means±SEM (n=6). The symbol * represents p<0.05 vs. normoxia.

FIGS. 11A-B are graphs showing differences between values obtained during normoxia and the first and second hour of hypoxia in controls for the dose-response effect of acetazolamide on delta mean pulmonary artery pressure (FIG. 11A) and delta pulmonary vascular resistance (FIG. 11B). Control, iv AZ (2 mg/kg), and po AZ (5 mg/kg) and the iv AZ (10 mg/kg) taken from applicant's earlier study (See Höhne C., et al., *J Appl Physiol* 97:515-521 (2004), which is hereby incorporated by reference in its entirety). Values are means±SEM (n=6). The symbol * represents p<0.05 vs. normoxia.

DETAILED DESCRIPTION OF THE INVENTION

One aspect of the present invention is directed to a method of treating a subject for a pulmonary disease by administering a therapeutically effective amount of a compound of the formula:

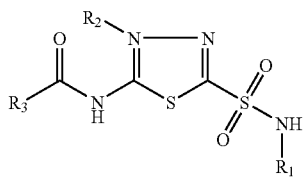

where $R_1$, $R_2$, and $R_3$ are each independently selected from the group consisting of hydrogen, a $C_1$ to $C_6$ alkyl, a halogen, a sulfate, and a phosphate. The pulmonary disease can be hypoxic pulmonary vasoconstriction, pulmonary edema, pulmonary hypertension, asthma, chronic obstructive pulmonary disease, cystic fibrosis, interstitial fibrosis, high altitude residence, sleep apnea syndrome, atrial septal defects, and pulmonary diseases associated with other conditions.

As used above, and throughout the description of the present invention, the following terms, unless otherwise indicated, shall be understood to have the following meanings.

The term "alkyl" means an aliphatic hydrocarbon group which may be straight or branched having about 1 to 6 carbon atoms in the chain. Branched means that one or more of the lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

In a preferred embodiment, the subject is human.

The compounds of the present invention can be administered orally, parenterally, for example, subcutaneously, intravenously, intramuscularly, intraperitoneally, by intranasal instillation, by inhalation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention may also be administered directly to the airways in the form of a dry powder. For use as a dry powder, the compounds of the present invention may be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose.

Suitable powder compositions include, by way of illustration, powdered preparations of the active ingredients thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants and co-solvents and may be filled into conventional aerosol containers that are closed by a suitable metering valve.

Another aspect of the present invention relates to a method of blocking hypoxic pulmonary vasoconstriction and/or preventing high altitude pulmonary edema in a subject. This is carried out by administering a compound which is not a carbonic acid inhibitor and has the formula:

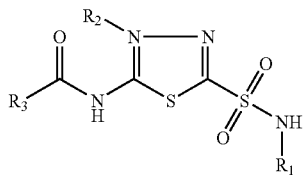

where $R_1$, $R_2$, and $R_3$ are each independently selected from the group consisting of hydrogen, a $C_1$ to $C_6$ alkyl, a halogen, a sulfate, or a phosphate. Such administration is carried out under conditions effective to block hypoxic pulmonary vasoconstriction and/or prevent high altitude pulmonary edema in the subject. This method can be carried out using the formulations and modes of administration described above.

A further aspect of the present invention pertains to an inhalable composition comprising a compound of the formula:

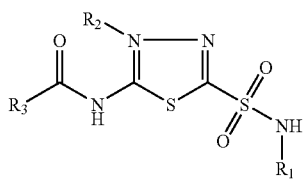

wherein $R_1$, $R_2$, and $R_3$ are each independently selected from the group consisting of hydrogen, a $C_1$ to $C_6$ alkyl, a halogen, a sulfate, or a phosphate, and an inhalable carrier for the compound. This method can be carried out using the formulations and modes of administration described above.

The present invention is also directed to a compound which is not a carbonic acid inhibitor and has the formula:

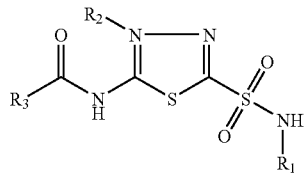

where $R_1$ and $R_2$ each independently are a $C_1$ to $C_6$ alkyl. This method can be carried out using the formulations and modes of administration described above.

EXAMPLES

Example 1

Isolation of Pulmonary Artery Smooth Muscle Cells (PASMC)

The method for obtaining single PASMCs has been described previously in Shimoda L. A., et al., *Am J Physiol* 274: 842-853 (1998), which is hereby incorporated by reference in its entirety. Intrapulmonary arteries (200-600 μm o.d.) were isolated from male Wistar rats (250-350 g) and cleaned of connective tissue. After the lumen was gently rubbed with a cotton swab to remove the endothelial cells, the arteries were allowed to recover for 30 minutes in cold (4° C.) HBSS containing (in mM): 130 NaCl, 5 KCl, 1.2 $MgCl_2$, 1.5 $CaCl_2$, 10 N-[2-hydroxyethyl]piperazine-N'-[2-ethanesulfonic acid] (HEPES) and 10 glucose, with pH adjusted to 7.2 with 5 M NaOH, followed by 20 minutes in reduced-$Ca^{2+}$ (20 μM $CaCl_2$) HBSS at room temperature. The tissue was enzymatically digested in reduced-$Ca^{2+}$ HBSS containing collagenase (type I; 1750 U/ml), papain (9.5 U/ml), bovine serum albumin (2 mg/ml) and dithiothreitol (1 mM) at 37° C. for 20 minutes. Following digestion, single smooth muscle cells were dispersed by gentle trituration with a wide-bore transfer pipette in $Ca^{2+}$-free HBSS and the cell suspension was placed on 25 mm glass cover slips. PASMCs were transiently cultured in Ham's-F-12 media supplemented with 0.5% fetal bovine serum and 1% penicillin/streptomycin for 24-48 hrs. before study.

Example 2

Measurement of $[Ca^{2+}]_i$

The methods for measurement of $[Ca^{2+}]_i$ have been described previously in Wang J., et al., *Am J Physiol Lung Cell Mol Physiol* 288: L1059-1069 (2005), which is hereby incorporated by reference in its entirety. Acute hypoxia increases intracellular $[Ca^{2+}]$ in pulmonary arterial smooth muscle by enhancing capacitative $Ca^{2+}$ entry. Briefly, PASMCs were placed in a laminar flow cell chamber and perfused with modified Kreb's bicarbonate solution containing (in mM): 118.3 NaCl, 4.7 KCl, 1.2 $MgSO_4$, 25 $NaHCO_3$, 1.1 glucose and 1.2 $KH_2PO_4$. $[Ca^{2+}]_i$ was measured in cells incubated with 5 μM Fura-2 AM for 60 min at 37°, then washed with PSS for 15 min at 37° C. to remove extracellular dye and allow complete de-esterification of cytosolic dye.

Ratiometric measurement of fluorescence from the dye was performed on a workstation (Intracellular Imaging Inc, Cincinnati, Ohio) consisting of a Nikon TSE 100 Ellipse inverted microscope with epi-fluorescence attachments. The light beam from a xenon arc lamp was filtered at 340 and 380 nm, and focused onto the PASMCS under examination via a 20× fluorescence objective (Super Fluor 20, Nikon). Light emitted from the cell at 510 nm was returned through the objective and detected by a cooled CCD imaging camera. An electronic shutter (Sutter Instruments) was used to minimize photobleaching of dye. Protocols were executed and data collected on-line with InCyte software (Intracellular Imaging Inc). $[Ca^{2+}]_i$ was estimated from in vitro calibration solutions.

Example 3

Measurement of $pH_i$ $pH_i$ within PASMCs was monitored using the cell permeant pH sensitive dye 2',7'-bis(carboxyethyl)-5(6)-carboxyflourescein (BCECF-AM). Cells were incubated with BCECF-AM for 60 min at 37° C. under an atmosphere of 21% $O_2$-5% $CO_2$. Cells were then washed with Kreb's solution for 15 min at 37° C. to remove extracellular dye and allow complete de-esterification of cytosolic dye. Cells were excited with light at 490 and 440 nm and light emitted from the cells was detected at 530 nm. The ratio of 490 to 440 nm emission was calculated and converted into pH values by performing a calibration curve after each experiment. PASMCs were subjected to a high $K^+$ buffer containing 10 µM nigericin, which allowed the cell to adopt the pH of the high $K^+$ buffer. Two high $K^+$/nigericin buffers were used to set pH to 6.5 or 7.5, $pH_i$ was estimated from in situ calibration after each experiment. Cells were perfused with a solution containing (in mM): 105 KCl, 1 $MgCl_2$, 1.5 $CaCl_2$, 10 glucose, 20 HEPES-Tris and 0.01 nigericin to allow $pH_i$ to equilibrate to external pH as in Quinn D. A., et al., *Am J Respir Cell Mol Biol* 5: 586-591 (1991), which is hereby incorporated by reference in its entirety. A two point calibration was created from fluorescence measured as $pH_i$ was adjusted with KOH from 6.5 to 7.5. Intracellular $H^+$ ion concentration ($[H^+]_i$) was determined from $pH_i$ using the formula: $pH_i=-\log([H^+]_i)$.

Example 4

Measurement of Changes in Membrane Potential

Changes in membrane potential were measured using the fluorescence dye, DiBAC4(3), which was excited at 490 nm and detected at 510 nm. Cells were loaded by continuous perfusion with Kreb's solution containing 500 nM DiBAC4(3) and were perfused for at least 15 minutes before beginning measurements to insure stable uptake of dye. Baseline DiBAC4(3) fluorescence was monitored for 5 minutes with control Kreb's, followed by 10 minutes with Kreb's in the presence or absence of AZ (100 µM). At the end of this period, cells were challenged with KCl (60 mM) or endothelin-1 (ET-1) ($10^{-8}$ M). Since DiBAC4(3) is a single wavelength dye, any change in the concentration of the dye in the perfusion medium (i.e., differing concentrations between perfusion reservoirs) could result in a change in fluorescence that is not due to a change in membrane potential. To minimize the possibility of this type of error, all experiments were performed using inflow from a single reservoir into which AZ, KCl or ET-1 were dissolved directly.

Example 5

Carbonic Anhydrase Inhibitors

Acetazolamide and ethoxzolamide (EZ) were obtained from Sigma Scientific. Benzolamide (BZ) was obtained from Dr. Thomas H. Maren, University of Florida Department of Pharmacology. The synthesis and purification of N-Meth-AZ followed that described in Maren T. H., *J Pharmacol Expt Therap* 117: 385-401 (1956), which is hereby incorporated by reference in its entirety. In N-Meth-AZ, one of the amine hydrogens of the sulfonamide moiety ($SO_2NH_2$) responsible for CA inhibition by AZ is replaced with a methyl group ($SO_2NHCH_3$) to prevent binding to CA, but otherwise leaves the rest of the molecule unaltered in terms of its general size, aromatic ring structure, and charge characteristics. FIG. 1 shows the chemical structures of the four sulfonamides, molecular weight, inhibition constant against carbonic anhydrase, lipid/water solubilities and ionization constants ($pK_a$).

Example 6

Effect of Hypoxia and AZ on $pH_i$

To test whether the mechanism by which AZ inhibited hypoxic pulmonary vasoconstriction in isolated lungs involved modulation of hypoxia-induced changes in PASMC $pH_i$, $pH_i$ was measured during control conditions, and after changing to hypoxic solution in the absence and presence of 100 µM AZ (FIG. 2). AZ alone caused a small, but statistically significant decrease in resting $pH_i$, from 7.26±0.02 to 7.22±0.03 (n=82 cells). Exposure to 4% $O_2$ had no significant effect on PASMC $pH_i$, with $pH_i$ measured at 7.23±0.02 during normoxia and 7.24±0.03 after 15 minutes of hypoxia. Similarly, hypoxia had no effect on $pH_i$ in PASMCs pretreated with AZ (7.22±0.03 to 7.24±0.03).

Example 7

Effect of Hypoxia and AZ on $[Ca^{2+}]_i$

Perfusing cells with solution equilibrated with 4% $O_2$, 5% $CO_2$ produced a rapid, reversible increase in $[Ca^{2+}]_i$ (FIG. 3). $[Ca^{2+}]_i$ increased 81.9±9.5 nM, from 176.2±10.2 nM to a maximum of 258.5±13.9 nM. The maximum change in $[Ca^{2+}]_i$ in response to hypoxia occurred within 7 minutes of beginning perfusion with hypoxic solution. Upon return to normoxia, $[Ca^{2+}]_i$ rapidly returned to normoxic levels.

Application of AZ (10-100 µM) had no effect on resting $[Ca^{2+}]_i$ in PASMCs (Table 1).

TABLE 1

Table 1. Effect of 3 different CA inhibitors (AZ = acetazolamide; BZ = benzolamide; and EZ = ethoxzolamide) at a concentration of 100 µM on basal intracellular $Ca^{2+}$ concentration and pH in PASMCs.

|  | Baseline | Treatment |
| --- | --- | --- |
| $[Ca^{2+}]_i$ (nM) |  |  |
| AZ (n = 73) | 159.6 ± 10.8 | 155.0 ± 9.6 |
| BZ (n = 50) | 113.4 ± 7.4 | 120.7 ± 7.7 |
| EZ (n = 88) | 125.5 ± 7.1 | 122.5 ± 6.3 |

TABLE 1-continued

Table 1. Effect of 3 different CA inhibitors (AZ = acetazolamide; BZ = benzolamide; and EZ = ethoxzolamide) at a concentration of 100 μM on basal intracellular $Ca^{2+}$ concentration and pH in PASMCs.

|  | Baseline | Treatment |
|---|---|---|
| $pH_i$ |  |  |
| AZ (n = 55) | 7.26 ± 0.02 | 7.22 ± 0.03 * |
| BZ (n = 48) | 7.31 ± 0.02 | 7.25 ± 0.03 * |
| EZ (n = 51) | 7.28 ± 0.04 | 7.19 ± 0.04 * |

* indicates significant difference from baseline (p < 0.05).

At 100 μM AZ, basal $[Ca^{2+}]_i$ was 159.6±10.8 nM prior to, and 150.0±9.6 nM after, 10 min of perfusion with AZ. AZ caused a concentration dependent-decrease in the hypoxia-induced rise in $[Ca^{2+}]_i$, with a significant reduction in the peak change in $[Ca^{2+}]_i$ induced by hypoxia at both 30 and 100 μM AZ (FIG. 3). From the concentration-inhibition plot, the $IC_{50}$ was estimated to be 50 μM.

Example 8

Effect of AZ on KCl-Induced $Ca^{2+}$ Responses

In order to examine whether the effect of AZ on hypoxia-induced $Ca^{2+}$ responses was due to a nonspecific inhibition of $Ca^{2+}$ signaling, the effect of AZ on the response to KCl was determined. Exposure to KCl (60 mM) caused a significant increase in $[Ca^{2+}]_i$ (153.2±14.5 to 276.6±19.8 nM; n=40 cells), reaching a mean peak change in $[Ca^{2+}]_i$ of 123.4±20.6 nM (FIG. 4). Following pretreatment with 100 μM AZ, the mean change in $[Ca^{2+}]_i$ in response to KCl was not altered, reaching a mean of 134.7±18.2 nM (from 157.8±11.9 to 292.6±21.2 nM; n=43 cells).

Example 9

Effect of EZ and BZ on $Ca^{2+}$ Responses

Similar to the lack of effect of AZ on basal $[Ca^{2+}]_i$, neither EZ nor BZ altered resting $[Ca^{2+}]_i$ (Table 1, above). However, in contrast to the effects of AZ on $[Ca^{2+}]_i$ during hypoxia, neither EF (FIG. 5) nor BZ (FIG. 6) had a significant effect on the hypoxia-induced increase in $[Ca^{2+}]_i$ at any of the concentrations tested (10-100 μM). Whether these CA inhibitors altered basal $pH_i$ was tested next. Consistent with the effect of AZ on basal $pH_i$, both EZ and BZ caused a significant decrease in resting $pH_i$ (Table 1, above), suggesting that CA inhibition in PASMCs results in intracellular acidosis, but that this is not central to the effect of AZ in blocking the hypoxia-mediated rise in $[Ca^{2+}]$.

Example 10

Effect of N-Meth-AZ on Hypoxia-Induced $Ca^{2+}$ Responses

That EZ and BZ had no effect on the increase in $Ca^{2+}$ induced by hypoxia but still caused intracellular acidosis suggested that AZ was acting via a mechanism independent of CA inhibition. In order to test this hypothesis, a synthesized compound in which the sulfonamide group responsible for CA inhibition was substituted with a methyl group (N-Meth-AZ) was used. The purity of the compound was assessed by high resolution FAB mass spectrometry, which showed only one species to be present in the recrystallized sample. In contrast to AZ, BZ and EZ, N-Meth-AZ (100 μM) had minimal effect on basal $pH_i$ (7.13±0.02 to 7.12±0.01; n=81 cells; FIG. 7). Pretreatment with N-Meth-AZ for 10 minutes caused a very small, but statistically significant increase in basal $[Ca^{2+}]_i$ (193.4±11.0 to 200.9±11.3 nM; n=63 cells). The increase in $[Ca^{2+}]_i$ induced by hypoxia in control PASMCs was markedly reduced in PASMCs treated with N-Meth-AZ, from 141.1±32.2 nM (n=78 cells) to 33.2±17.4 nM (n=63 cells) (FIGS. 8A-C). In order to test whether the inhibitory effect of N-Meth-AZ on hypoxia-induced $Ca^{2+}$ responses was due to generalized cell toxicity, the effect of N-Meth-AZ on KCl-induced $Ca^{2+}$ responses was also tested. The mean increase in $[Ca^{2+}]_i$ in response to KCl (100 mM) was similar in the presence and absence of 100 μM N-Meth-AZ (FIGS. 8D-F).

Example 11

Effect of AZ on $E_m$

AZ has recently been proposed to alter the activation of $Ca^{2+}$-activated $K^+$ channels, causing hyperpolarization. See Pickkers P., et al., *Br J Pharmacol* 132: 443-450 (2001); Tricarico D., et al., *Ann Neurol* 48: 304-312 (2000); and Tricarico D., et al., *Faseb J* 18: 760-761 (2004), which are hereby incorporated by reference in their entirety. Since depolarization is believed to contribute to the hypoxia-induced increase in $[Ca^{2+}]_i$, AZ-induced hyperpolarization could prevent activation of voltage-gated $Ca^{2+}$ channels and an increase in $[Ca^{2+}]_i$ in response to hypoxia. In order to test this possibility, the $E_m$-sensitive fluorescent dye, DiBAC4(3) was used. The ability of the dye to measure changes in $E_m$ was first verified by measuring the response to 1) the $K^+$ channel opener, pinacidil, which causes hyperpolarization; 2) KCl, which causes depolarization by reducing the gradient for $K^+$ efflux and 3) ET-1, which causes depolarization via inhibition of $K^+$ channels (FIG. 9). Baseline fluorescence was relatively stable over time, decreasing by 4.11±0.4% over 10 minutes (n=90 cells). In response to pinacidil (100 μM), fluorescence decreased 19.76±3.3% (n=58 cells), whereas fluorescence increased 61.58±12.8% in response to 60 mM KCl (n=109 cells) and 75.6±13.4% in response to ET-1 (n=82 cells). Application of AZ (100 μM) had no significant effect on basal $E_m$ (−2.86±4.5%; n=108 cells), and did not alter the increase in fluorescence induced by either KCl (53.13±14.8%; n=90 cells) or ET-1 (66.0±10.4%; n=87 cells).

Inhibition of CA with AZ, BZ or EZ caused a small but significant acid shift in PASMC $pH_i$, consistent with a mild acidosis arising from loss of CA-mediated facilitated $CO_2$ diffusion. See Swenson E. R., *Eur Respir J* 12: 1242-1247 (1998), which is hereby incorporated by reference in its entirety. Challenge with moderate hypoxia caused a significant increase in PASMC $[Ca^{2+}]_i$, that was prevented by AZ, but not BZ or EZ. The lack of effect of BZ and EZ on the hypoxic response was not due to ineffective concentrations of these two more powerful CA inhibitors, as both reduced basal $pH_i$ to a similar, or greater, extent than did AZ. Moreover, N-Meth-AZ, which has no CA inhibiting action and had no effect on $pH_i$, also prevented the hypoxia-induced increase in $[Ca^{2+}]_i$. The inhibitory action of AZ and N-Meth-AZ on $Ca^{2+}$ signaling was specific for hypoxia, as no effect on KCl-induced $Ca^{2+}$ responses was observed. Finally, AZ had no effect on either resting $E_m$ or agonist-induced depolarization. These results suggest that AZ prevents a rise in $[Ca^{2+}]_i$ in response to hypoxia in PASMCs by a mechanism that does not involve acidification of $pH_i$ or a change in membrane potential and is independent of CA inhibition.

CA inhibitors were originally developed as diuretics with primary action on the kidney to interfere in acid-base related ion transport events. Although their use as diuretics has been supplanted by more potent alternatives, they are presently used to treat glaucoma, metabolic alkalosis, epilepsy and acute mountain sickness, conditions in which alteration in systemic acid-base status or CA dependent ion transport can be beneficial. Carbonic anhydrase is expressed in most cells and there have been 14 different isozymes identified. This rich diversity of expression has led some to search for non-classical (i.e. non acid-base) functions of the enzyme. Swenson E. R., et al., *J Clin Invest* 92: 702-709 (1993), which is hereby incorporated by reference in its entirety, showed that CA inhibition impairs ventilation-perfusion matching in the lung, a process that is dependent upon both $O_2$ and $CO_2$ dependent changes in bronchial and vascular smooth muscle tone. In order to directly test whether CA inhibition alters HPV, the major mechanism that maintains $V_A/Q$ matching, Deem et al. found that AZ blunts and slows HPV in the isolated perfused rabbit lung. See Deem S., et al., *Respir Physiol* 123: 109-119 (2000), which is hereby incorporated by reference in its entirety. Itturiaga et al. found similar effects on another hypoxia-sensitive response; the neural output of the peripheral receptors of the carotid body, which contain CA, as does vascular smooth muscle. See Iturriaga R., et al., *Am J Physiol* 261: C565-573 (1991); and Berg J. T., et al., *J Histochem Cytochem* 52: 1101-1106 (2004), which are hereby incorporated by reference in their entirety.

The mechanism by which AZ prevents HPV in vivo may be multifactorial. The respiratory stimulation generated by an induction of metabolic acidosis leads to increased ventilation and enhanced alveolar $PO_2$, and thus a reduction of the primary stimulus to HPV. See Swenson E. R., *Eur Respir J* 12: 1242-1247 (1998), which is hereby incorporated by reference in its entirety. However, the prevention of HPV by AZ in isolated perfused lung preparations and awake animals, where ventilation and/or alveolar $PO_2$ are carefully controlled, establishes that this is not necessary and demonstrates that there is a direct action of AZ in reducing the hypoxic sensitivity of the pulmonary vasculature. See Deem S., et al., *Respir Physiol* 123: 109-119 (2000); Emery C. J., et al., *Bull Eur Physiopathol Respir* 13: 763-776 (1977); and Hohne C., et al., *J Appl Physiol* 97: 515-521 (2004), which are hereby incorporated by reference in their entirety.

The results from the current study, performed on isolated PASMCs extend these findings in several important ways. First, the results show that AZ acts directly on the vascular smooth muscle thus eliminating the mediation of the vascular endothelium or alveolar epithelium, which also contain carbonic anhydrase. See Swenson E. R., *Eur Respir J* 12: 1242-1247 (1998), which is hereby incorporated by reference in its entirety. Second, it is now demonstrated that despite the presence of CA in vascular smooth muscle, the effect of AZ on HPV does not depend upon CA inhibition, or upon intracellular acidification. All three CA inhibitors (AZ, BZ and EZ) resulted in a small but significant acid shift in basal $pH_i$ in cells. This is consistent with CA inhibition-induced acidosis described in corneal endothelium, nonpigmented ciliary epithelium, lactotrophs, neuronal cells and rat heart, brain, liver and spleen tissue. See Bonanno J. A., et al., *Exp Eye Res* 60: 425-434 (1995); Wu Q., et al., *J Membr Biol* 162: 31-38 (1998); Garcia L., et al., *Endocrinology* 138: 4191-4198 (1997); Lamsa K. et al., *J Neurophysiol* 78: 2582-2591 (1997); Leniger T., et al., *Epilepsia* 43: 469-474 (2002); and Rothe K. F. et al., *Acta Anaesthesiol Scand* 30: 566-570 (1986), which are hereby incorporated by reference in their entirety. And it rules out the possibility that at least in the case of highly diffusible EZ, that there was a lack of intracellular penetration of the drug. These findings suggest that CA is present in PASMCs and actively participates in regulation of basal $pH_i$ under normal conditions.

That AZ decreased $pH_i$ in PASMCs presented a possible mechanism for preventing HPV. Intracellular pH can modulate a number of cell functions, including PASMC contraction. For example, increasing intracellular pH with $NH_4Cl$ caused contraction in isolated canine pulmonary arteries and cultured ferret smooth muscle and an increase in pulmonary arterial pressure in isolated perfused lungs. See Farrukh I. S., et al., *J Appl Physiol* 80: 496-505 (1996); and Krampetz I. K. et al., *Am J Physiol* 260 L516-521 (1991), which are hereby incorporated by reference in their entirety. With respect to hypoxia, the effects of $pH_i$ on HPV have been somewhat controversial, although a number of studies have suggested a role for alkaline $pH_i$. For example, while no change in $pH_i$ was observed when oxygen concentration was reduced, consistent with reports in systemic vascular smooth muscle, previous studies from other labs have demonstrated that moderate hypoxia causes alkalinization of isolated, cultured smooth muscle cells from small diameter (<600 microns) feline pulmonary arteries. See Foy R. A., et al., *Circ Res* 80; 21-27 (1997); Gebremedhin D., et al., *Pflugers Arch* 428: 621-630 (1994); and Shimizu S., et al., *Circ Res* 86: 862-870 (2000), which are hereby incorporated by reference in their entirety. Cells from large diameter arteries (>800 microns), which do not contract in response to hypoxia, exhibited a reduction in $pH_i$. See Madden J. A., et al. *Am J Physiol Lung Cell Mol Physiol* 280: L264-271 (2001), which is hereby incorporated by reference in its entirety. A similar decrease in $pH_i$ was observed in proximal porcine arteries during hypoxic relaxation, with recovery of $pH_i$ toward normal levels occurring during the late sustained contractile phase. See Leach R. M., et al., *Am J Physiol Lung Cell Mol Physiol* 278: L294-304 (2000), which is hereby incorporated by reference in its entirety. Moreover, HPV in isolated perfused rat lungs was enhanced when intracellular $pH_i$ was increased by addition of weak bases, whereas decreasing $pH_i$ by addition of weak acids or by inhibition of $Na^+/H^+$ exchange blunted HPV. See Raffestin B. et al., *J Appl Physiol* 63: 2524-2531 (1987), which is hereby incorporated by reference in its entirety.

If alkalinization of PASMCs during hypoxia contributes to HPV, a decrease in $pH_i$, as seen with CA inhibitors, could have adverse effects on HPV and could provide a mechanism for AZ-induced antagonism of HPV. This hypothesis is opposed, however, by results from experiments that were performed to assess the effect of CA inhibition on PASMC $Ca^{2+}$ signaling during hypoxia. In PASMCs, hypoxia caused a significant, rapid and reversible increase in $[Ca^{2+}]_i$. This increase in $[Ca^{2+}]_i$ in response to hypoxia had previously been shown to require $Ca^{2+}$ influx and was required for generation of HPV. See Bakhramov A., et al., *Exp Physiol* 83: 337-347 (1998); Cornfield D. N., et al., *Am J Physiol* 266: L469-475 (1994); Urena J., et al., *J Physiol* 496 (Pt 1): 103-109 (1996); McMurtry I. F., et al., *Circ Res* 38: 99-104 (1976); Naeije R., et al., *Chest* 82: 404-410 (1982); Redding G. J., et al., *Am Rev Respir Dis* 129: 785-789 (1984); Simonneau G., et al., *N Engl J Med* 304: 1582-1585 (1981); Stanbrook H. S., et al., *Am Rev Respir Dis* 130: 81-85 (1984); Suggett A. J., et al., *Clin Exp Pharmacol Physiol* 7: 263-274 (1980); and Tucker A., et al., *Proc Soc Exp Biol Med* 151: 611-614 (1976), which are hereby incorporated by reference in their entirety. It was found that AZ inhibited the rise in $[Ca^{2+}]_i$ induced by hypoxia, suggesting an ability to modulate $Ca^{2+}$ signaling.

The effect of AZ was concentration dependent, with a calculated $IC_{50}$ of 50 μM. This concentration corresponds to the concentrations of AZ that inhibited HPV in isolated lungs and intact animals, see Deem S., et al., *Respir Physiol* 123: 109-119 (2000); and Emery C. J., et al., *Bull Eur Physiopathol Respir* 13: 763-776 (1977), which are hereby incorporated by reference in their entirety. In contrast, neither BZ nor EZ was able to alter the hypoxia-induced change in $[Ca^{2+}]_i$, yet caused similar, if not greater, acidification of PASMCs.

Further investigated was the possibility that the effects of AZ on HPV and hypoxia-induced $Ca^{2+}$ responses were independent of CA inhibition using N-Meth-AZ. As expected, substitution of one of the amines in the sulfonamide group with a methyl group resulted in a loss of ability of the compound to induce acidification. However, N-Meth-AZ reduced the increase in $[Ca^{2+}]_i$ in response to hypoxia to a similar extent as the same concentration of AZ. Based on the data, inhibition of CA and consequent acidification can be ruled out as the mechanism by which AZ prevents HPV and hypoxic $Ca^{2+}$ signaling.

The mechanism by which AZ inhibits hypoxia-induced $Ca^{2+}$ mobilization in PASMCs is unclear. Inhibitors of CA have been shown to block a range of voltage-dependent $Ca^{2+}$ channels, some of which have been shown to participate in HPV. See Gottfried J. A. et al., *J Neurophysiol* 74: 2774-2777 (1995); Jahromi S. S., et al., *Brain Res* 872: 20-28 (2000); McNaughton N. C., et al., *J Pharmacol Sci* 95: 240-247 (2004); Zhang X., et al., *Epilepsia* 41 Suppl 1: S52-60 (2000); Bakhramov A., et al., *Exp Physiol* 83: 337-347 (1998); McMurtry I. F., et al., *Circ Res* 38: 99-104 (1976); Naeije R., et al., *Chest* 82: 404-410 (1982); Redding G. J., et al., *Am Rev Respir Dis* 129: 785-789 (1984); Simonneau G., et al., *N Engl J Med* 304: 1582-1585 (1981); Stanbrook H. S., et al., *Am Rev Respir Dis* 130: 81-85 (1984); Suggett A. J., et al., *Clin Exp Pharmacol Physiol* 7: 263-274 (1980); and Tucker A., et al., *Proc Soc Exp Biol Med* 151: 611-614 (1976), which are hereby incorporated by reference in their entirety. In addition to hypoxia, the ability of AZ and N-Meth-AZ to inhibit KCl-induced $Ca^{2+}$ mobilization was also tested. KCl is a nonspecific vasoconstrictor that induces an increase in $[Ca^{2+}]_i$ in PASMCs that has been shown to be dependent on membrane depolarization and $Ca^{2+}$ influx through voltage-gated $Ca^{2+}$ channels. See Shimoda L. A., et al., *Am J Physiol Lung Cell Mol Physiol* 279: L884-894 (2000); and Wang J., et al., *Am J Physiol Lung Cell Mol Physiol* 288: L1059-1069 (2005), which are hereby incorporated by reference in their entirety. In PASMCs, the KCl-induced increase in $[Ca^{2+}]_i$ was similar in magnitude to that induced by hypoxia, but was unaffected by pretreatment with AZ or N-Meth-AZ. These results indicate that AZ had no effect on the activation of voltage-gated $Ca^{2+}$ channels and suggest that the effect of AZ on PASMC $Ca^{2+}$-signaling during hypoxia was not due to toxicity or a nonspecific or generalized inability to mobilize intracellular $Ca^{2+}$. The differential inhibitory effect of AZ on the increases in $[Ca^{2+}]_i$ in response to hypoxia and KCl might also point to the intriguing implication that hypoxia causes $Ca^{2+}$ influx through mechanisms in addition to L-type $Ca^{2+}$ channels, a possibility recently suggested in studies by Wang J., et al., *Am J Physiol Lung Cell Mol Physiol* 288: L1059-1069 (2005), which is hereby incorporated by reference in its entirety.

AZ has been proposed to cause membrane hyperpolarization which could act to decrease $Ca^{2+}$ influx through voltage-gated $Ca^{2+}$ channels in PASMCs. See Chipperfield A. R., et al., *Biochem Biophys Res Commun* 194: 407-412 (1993); Pickkers P. et al., *Hypertension* 33: 1043-1048 (1999); Pickkers P., et al., *Br J Pharmacol* 132: 443-450 (2001); and Tricarico D., et al., *Faseb J* 18: 760-761 (2004), which are hereby incorporated by reference in their entirety. AZ was found to have no effect on resting $E_m$ in the cells, results consistent with findings in rat kidney. See Hohne C., et al., *J Appl Physiol* 97: 515-521 (2004), which is hereby incorporated by reference in its entirety. The lack of a measurable effect of AZ on $E_m$ was not due to an inability to detect hyperpolarization in the system, as a decrease in cell fluorescence was readily observed in response to pinacidil, a $K^+$ channel activator. In studies demonstrating AZ-induced hyperpolarization secondary to activation of $Ca^{2+}$-activated $K^+$ ($K_{Ca}$) channels, it was found that AZ enhanced $K_{Ca}$ currents when the channels were already open: however, unlike other systemic vascular smooth muscle, $K_{Ca}$ channels are not active under basal conditions, and thus do not contribute to regulation of resting membrane potential, in PASMCs from adult animals. See Knot H. J., et al., *J Physiol* 508 (Pt 1): 211-221 (1998); Tricarico D., et al., *Ann Neurol* 48: 304-312 (2000); Archer S. L., et al. *Circ Res* 78: 431-442 (1996); Shimoda L. A., et al., *Am J Physiol* 274: L842-853 (1998); and Yuan X. J., *Circ Res* 77: 370-378 (1995), which are hereby incorporated by reference in their entirety. It is also possible that the effect of AZ on $K_{Ca}$ channels is cell specific and that the mechanism required for AZ-induced enhancement of $K_{Ca}$ currents is not active or present in PASMCs. Other indirect evidence that would point away from AZ-induced hyperpolarization as the mechanism for repressed $Ca^{2+}$ signaling would be that in previous studies, EZ was as effective as AZ in opening $K_{Ca}$ channels (see Tricarico D., et al., *Ann Neurol* 48: 304-312 (2000), which is hereby incorporated by reference in its entirety), but had no effect on the hypoxia-induced rise in $[Ca^{2+}]_i$ in the cells. It is also unlikely that AZ acts to repress depolarization in response to agonists by preventing inhibition of $K^+$ channels since AZ did not alter depolarization in response to ET-1, which like hypoxia, causes depolarization in large part via inhibition of voltage-gated $K^+$ channels. See Archer S. L., et al., *Circ Res* 73: 1100-1112 (1993); Yuan X. J., et al., *Exp Physiol* 80: 803-813 (1995); and Shimoda L. A., et al. *Am J Physiol* 274: L842-853 (1998), which are hereby incorporated by reference in their entirety. Moreover, AZ also had no effect on changes in $E_m$ in response to KCl, which causes depolarization by reducing the gradient for $K^+$ efflux, indicating that AZ does not activate alternate (non-$K^+$ channel) hyperpolarization pathways in the cells.

In summary, it was found that AZ blocks the rise in intracellular calcium that occurs with hypoxic exposure in PASMCs by a mechanism independent of CA inhibition and its generation of a mild intracellular acidosis. AZ does not appear to exert its inhibitory effect on the hypoxia-mediated increase in $[Ca^{2+}]$ in PASMCs by either changes in $E_m$ or by blockade of voltage-sensitive membrane L-type calcium channels. The molecular target or pathway that is altered by AZ, but not other sulfonamide CA inhibitors, and is responsible for HPV inhibition, remains to be discovered. Elucidation of the action of AZ in blunting HPV by compounds such as N-Meth-AZ, which are similar in structure to AZ but lack its CA inhibiting activity (and attendant side effects), may yield new therapeutic options in treatment and prevention of HAPE and other forms of pulmonary hypertension.

Example 12

Dog Studies

A total of 30 experiments were performed on six female Beagle dogs (body wt 14.3±0.3 kg). The dogs were kept under highly standardized conditions and received a standardized diet five days before the experiments. The preparation and catheterization of the conscious dog were performed according to former experiments as in Höhne C., et al., *J Appl Physiol* (2004), which is hereby incorporated by reference in its entirety. To permit spontaneous breathing through a low resistance circuit, a face mask was attached, which enclosed the dog's snout in a leak proof fashion. This custom made mask is equipped with a 2.5 cm ID connector to connect it to a ventilator set to CPAP mode (3 4 cmH$_2$0) (Servo900C; Siemens-Elema, Erlangen/Germany).

Six dogs were studied in five different protocols in randomized order:
1) Controls.
2) Acetazolamide (Diamox®, Lederle, Wolfratshausen/Germany) intravenously (iv AZ): Bolus AZ (2 mg/kg), followed by a continuous infusion of 2 mg·kg$^{-1}$·h$^{-1}$.
3) Acetazolamide orally (po AZ): 5 mg/kg acetazolamide orally 12 and 1 hr before the normoxic/hypoxic protocol.
4) Benzolamide intravenously: Bolus (2 mg/kg), followed by a continuous infusion of 2 mg·kg$^{-1}$·h$^{-1}$, a dosage which inhibits only renal and vascular endothelial extracellular CA, without affecting red cell CA as in Travis D. M., et al. *J Pharmacol Exp Ther* (1964), which is hereby incorporated by reference in its entirety.
5) Ethoxzolamide (Sigma-Aldrich, Steinheim/Germany) intravenously: Bolus ethoxzolamide (1 mg/kg), followed by a continuous infusion of 1 mg·kg$^{-1}$·h$^{-1}$. This lower dosage compared to iv AZ was chosen because ethoxzolamide is a 5-10 fold more potent CA inhibitor (FIG. 1) and its easy penetrance into the brain may induce more CNS acid-base changes and greater hyperventilation if used at equivalent doses.

Example 13

Control Experiments

In control experiments, the dogs breathed room air (21% O$_2$, 79% N$_2$; normoxia) for one hour, followed by breathing a gas mixture containing 10% O$_2$ and 90% N$_2$ for two hours (hypoxia). The time course was the same for the CA inhibitor experiments, but F$_I$O$_2$ was reduced to 0.09 during the hypoxia period to match the arterial and alveolar PO$_2$ of the control dogs, which otherwise would have been higher on 10% O$_2$ as a result of the known ventilatory stimulant effect of all CA inhibitors. See Höhne C., et al., *J Appl Physiol* 97:515-521 (2004), which is hereby incorporated by reference in its entirety. The hemodynamic measurements (arterial blood pressure, heart rate, central venous pressure, pulmonary artery pressure, pulmonary capillary wedge pressure), minute ventilation, renal function data, time points for blood samples for blood gases, actual bicarbonate, base excess, plasma electrolytes and hormones, measurements of plasma and urinary values were according to former studies. See Höhne C., et al., *J Appl Physiol* 90:1842-1848 (2001), which is hereby incorporated by reference in its entirety.

Example 14

Statistical Analysis

Values are given as means±SEM (n=6). For intra-group comparisons a general linear model of analysis of variance (GLM-ANOVA) for repeated measures was applied (NCSS97/PASS 2000, Saugus/MA, USA). Post-hoc testing of means was performed with Student's t-test. Level of significance for error of first order was adjusted according to Holm's procedure. Statistical significance was assumed at p<0.05.

Example 15

Arterial Blood Gases, Ventilation, and Acid-Base Status

During normoxia, P$_a$O$_2$ was greater and P$_a$CO$_2$ lower in iv AZ, po AZ, and ethoxzolamide protocols (p<0.05) compared to both control and benzolamide treated groups. These changes in blood gases are reflective of the higher ventilation in these groups. During hypoxia, P$_a$O$_2$ decreased to 35-39 mmHg in all dogs (p<0.05, FIG. 1), and P$_a$CO$_2$ decreased from 38-32 mmHg during normoxia to 24-29 mmHg during hypoxia (p<0.05, Table 2). Minute ventilation increased during hypoxia in all protocols (Table 2).

TABLE 2

Table 2. Arterial blood gases and minute ventilation in Controls, with iv AZ, po AZ, benzolamide, and ethoxzolamide during normoxia and hypoxia.

|  | Normoxia 1$^{st}$ h | Hypoxia 2$^{nd}$ h | Hypoxia 3$^{rd}$ h |
|---|---|---|---|
| Pa$_{O_2}$, Torr | | | |
| Controls | 94 ± 2 | 35 ± 1* | 36 ± 1* |
| iv AZ | 106 ± 3$^†$ | 37 ± 1* | 39 ± 1* |
| po AZ | 108 ± 2$^†$ | 37 ± 1* | 38 ± 1* |
| Benzolamide | 96 ± 1 | 37 ± 1* | 38 ± 1* |
| Ethoxzolamide | 105 ± 1$^†$ | 36 ± 1* | 38 ± 1* |
| Pa$_{CO_2}$, Torr | | | |
| Controls | 38 ± 1 | 31 ± 1* | 29 ± 1* |
| iv AZ | 34 ± 1$^†$ | 30 ± 1* | 28 ± 1* |
| po AZ | 32 ± 1$^†$ | 29 ± 1* | 27 ± 1* |
| Benzolamide | 37 ± 1 | 30 ± 1* | 29 ± 1* |
| Ethoxzolamide | 33 ± 1$^†$ | 26 ± 1*$^†$ | 24 ± 1*$^†$ |
| V$_E$, l/min | | | |
| Controls | 3.8 ± 0.4 | 5.7 ± 0.7 | 5.3 ± 0.7 |
| iv AZ | 4.0 ± 0.3 | 5.8 ± 0.6 | 7.0 ± 0.6* |
| po AZ | 4.5 ± 0.3 | 5.9 ± 0.2* | 6.1 ± 0.2* |
| Benzolamide | 3.0 ± 0.2 | 4.4 ± 0.5 | 5.1 ± 0.6* |
| Ethoxzolamide | 4.0 ± 0.2 | 6.4 ± 0.7 | 6.9 ± 0.9* |

PaO$_2$, arterial oxygen tension; PaCO$_2$, arterial carbon dioxide tension; V$_E$, minute ventilation. Values measured during one hour of normoxia and two hours of hypoxia. Means ± SEM, n = 6;
*P < 0.05 vs. normoxia,
$^†$P < 0.05 vs. Controls.

Changes in acid-base status are depicted in Table 3. With po AZ and ethoxzolamide base excess was about −4 to −5 mmol/l lower than in controls (p<0.05), but due to hyperventilation and consequently low P$_a$CO$_2$ values (Table 2, above), plasma pHa remained between 7.34 and 7.40 during normoxia and increased to 7.40-7.46 during hypoxia (Table 3), in conjunction with an increase in minute ventilation (Table 2, above).

TABLE 3

Table 3. Arterial pH, bicarbonate concentration, base excess and plasma potassium concentration in Controls, with iv AZ, po AZ., benzolamide, and ethoxzolamide during normoxia and hypoxia.

|  | Normoxia 1st h | Hypoxia 2nd h | Hypoxia 3rd h |
|---|---|---|---|
| $pH_a$ | | | |
| Controls | 7.39 ± 0.01 | 7.45 ± 0.01* | 7.46 ± 0.01* |
| iv AZ | 7.40 ± 0.01 | 7.42 ± 0.01 | 7.41 ± 0.01 |
| po AZ | 7.34 ± 0.01† | 7.40 ± 0.01* | 7.40 ± 0.01* |
| Benzolamide | 7.35 ± 0.01† | 7.41 ± 0.01* | 7.42 ± 0.01* |
| Ethoxzolamide | 7.37 ± 0.01† | 7.41 ± 0.01 | 7.42 ± 0.01 |
| $HCO_{3a}$, mM | | | |
| Controls | 22.4 ± 0.4 | 20.3 ± 1.2 | 20.0 ± 1.1 |
| iv AZ | 20.9 ± 0.6 | 19.0 ± 0.4* | 17.5 ± 0.5* |
| po AZ | 17.1 ± 0.7† | 17.6 ± 0.6 | 16.9 ± 0.5 |
| Benzolamide | 20.1 ± 0.3† | 18.4 ± 0.3* | 17.7 ± 0.4* |
| Ethoxzolamide | 19.6 ± 0.6† | 18.1 ± 1.3 | 17.6 ± 1.3 |
| $BE_a$, mM | | | |
| Controls | −1.7 ± 0.4 | −1.6 ± 0.6 | −2.4 ± 0.6 |
| iv AZ | −3.1 ± 0.5 | −4.0 ± 0.3 | −5.6 ± 0.5* |
| po AZ | −7.2 ± 0.6† | −5.8 ± 0.4† | −6.5 ± 0.4† |
| Benzolamide | −4.4 ± 0.4† | −4.4 ± 0.4 | −4.9 ± 0.4 |
| Ethoxzolamide | −5.3 ± 0.5† | −6.2 ± 1.2† | −6.7 ± 1.1† |
| $P_K$, mM | | | |
| Controls | 3.5 ± 0.1 | 3.2 ± 0.1 | 3.2 ± 0.1* |
| iv AZ | 3.0 ± 0.1† | 2.8 ± 0.1† | 2.8 ± 0.1† |
| po AZ | 2.9 ± 0.1† | 2.9 ± 0.1† | 2.9 ± 0.1 |
| Benzolamide | 3.0 ± 0.1† | 2.9 ± 0.1† | 2.8 ± 0.1† |
| Ethoxzolamide | 3.1 ± 0.1† | 2.8 ± 0.1*† | 2.7 ± 0.1*† |

$HCO_{3a}$, arterial actual bicarbonate concentration; $BE_a$, arterial base excess; $P_K$, plasma potassium concentration. Values measured during one hour of normoxia and two hours of hypoxia. Means ± SEM, n = 6;
*P < 0.05 vs. normoxia,
†P < 0.05 vs. Controls.

Example 16

Pulmonary and Systemic Hemodynamics

With iv AZ, mean pulmonary artery pressure (MPAP) and pulmonary vascular resistance (PVR) did not change during hypoxia (FIG. 10, Table 4), whereas MPAP and PVR both increased in controls, as well as with benzolamide and ethoxzolamide (p<0.05, FIG. 10, Table 4). With po AZ, MPAP increased slightly after 2 hrs of hypoxia whereas PVR did not change (Table 4). FIG. 11 combines the pulmonary hemodynamic data with acetazolamide in this study with that from a previous study with 10 mg/kg iv to better show the full drug dose response relationship, see Höhne C., et al., *J Appl Physiol* 97; 515-521 (2004), which is hereby incorporated by reference in its entirety.

TABLE 4

Table 4. Systemic and pulmonary hemodynamic parameters in Controls, with iv AZ, po AZ, benzolamide, and ethoxzolamide during normoxia and hypoxia.

|  | Normoxia 1st h | Hypoxia 2nd h | Hypoxia 3rd h |
|---|---|---|---|
| HR, beats/min | | | |
| Controls | 82 ± 5 | 101 ± 8 | 102 ± 9 |
| iv AZ | 70 ± 5 | 92 ± 9 | 98 ± 8 |
| po AZ | 78 ± 5 | 101 ± 9 | 103 ± 7 |
| Benzolamide | 73 ± 6 | 94 ± 10 | 90 ± 8 |
| Ethoxzolamide | 77 ± 4 | 104 ± 6* | 106 ± 4* |
| MAP, mmHg | | | |
| Controls | 99 ± 3 | 113 ± 6 | 112 ± 7 |
| iv AZ | 97 ± 4 | 109 ± 7 | 111 ± 6 |
| po AZ | 99 ± 1 | 110 ± 5 | 108 ± 7 |
| Benzolamide | 102 ± 5 | 109 ± 6 | 109 ± 9 |
| Ethoxzolamide | 96 ± 2 | 104 ± 7 | 101 ± 1 |
| CO, l/min | | | |
| Controls | 2.6 ± 0.1 | 3.0 ± 0.3 | 2.8 ± 0.2 |
| iv AZ | 2.4 ± 0.2 | 2.6 ± 0.2 | 2.4 ± 0.1 |
| po AZ | 2.5 ± 0.2 | 2.8 ± 0.2 | 2.7 ± 0.3 |
| Benzolamide | 2.7 ± 0.2 | 2.6 ± 0.2 | 2.7 ± 0.2 |
| Ethoxzolamide | 2.8 ± 0.2 | 2.9 ± 0.2 | 2.9 ± 0.3 |
| SVR, dyn · s$^1$ · cm$^{-5}$ | | | |
| Controls | 3039 ± 205 | 3106 ± 311 | 3200 ± 401 |
| iv AZ | 3347 ± 260 | 3348 ± 260 | 3675 ± 241 |
| po AZ | 3301 ± 320 | 3238 ± 326 | 3270 ± 380 |
| Benzolamide | 3101 ± 376 | 3272 ± 113 | 3227 ± 83 |
| Ethoxzolamide | 2784 ± 200 | 2745 ± 154 | 3270 ± 380 |
| CVP, cmH$_2$O | | | |
| Controls | 2.3 ± 0.4 | 1.8 ± 0.5 | 1.5 ± 0.6 |
| iv AZ | 1.8 ± 0.3 | 2.6 ± 0.6 | 1.8 ± 0.5 |
| po AZ | 2.0 ± 0.3 | 1.5 ± 0.2 | 1.3 ± 0.2 |
| Benzolamide | 1.8 ± 0.3 | 1.5 ± 0.2 | 1.2 ± 0.2 |
| Ethoxzolamide | 2.3 ± 0.2 | 2.5 ± 0.2 | 2.5 ± 0.2 |
| MPAP, mmHg | | | |
| Controls | 13 ± 1 | 20 ± 1* | 21 ± 1* |
| iv AZ | 14 ± 0 | 15 ± 1† | 14 ± 1† |
| po AZ | 12 ± 1 | 17 ± 1 | 17 ± 2* |
| Benzolamide | 12 ± 1 | 18 ± 1* | 19 ± 1* |
| Ethoxzolamide | 11 ± 1 | 17 ± 1* | 16 ± 1* |
| PVR, dyn · s$^{-1}$ · cm$^{-5}$ | | | |
| Controls | 303 ± 20 | 470 ± 39* | 498 ± 33* |
| iv AZ | 347 ± 31 | 373 ± 39 | 367 ± 34 |
| po AZ | 272 ± 20 | 349 ± 30 | 355 ± 42 |
| Benzolamide | 254 ± 6 | 449 ± 27* | 464 ± 44* |
| Ethoxzolamide | 221 ± 21† | 354 ± 19* | 368 ± 48* |
| PCWP, cm H$_2$O | | | |
| Controls | 3.3 ± 0.7 | 2.8 ± 0.2 | 3.5 ± 0.6 |
| iv AZ | 3.5 ± 0.6 | 3.5 ± 0.3 | 3.3 ± 0.2 |
| po AZ | 3.5 ± 0.3 | 3.3 ± 0.3 | 3.6 ± 0.4 |
| Benzolamide | 3.2 ± 0.2 | 3.2 ± 0.4 | 3.8 ± 0.3 |
| Ethoxzolamide | 3.8 ± 0.2 | 4.0 ± 0.5 | 3.5 ± 0.3 |

HR, heart rate; MAP, mean arterial pressure; CO, cardiac output; SVR, systemic vascular resistance; CVP, central venous pressure; MPAP, mean pulmonary arterial pressure; PVR, pulmonary vascular resistance; PCWP, pulmonary capillary wedge pressure. Values measured during one hour of normoxia and at 2 hours of hypoxia. Means ± SEM, n = 6;
*p < 0.05 vs. normoxia,
†p < 0.05 vs. Controls.

Heart rate increased slightly during hypoxia in all protocols (Table 4, above). Cardiac output, mean arterial pressure (MAP), systemic vascular resistance (SVR), central venous pressure (CVP) and pulmonary capillary wedge pressure (PCWP) did not change during hypoxia in any protocol, and were not different between the groups (Table 4, above).

Example 17

Plasma Hormones, Electrolytes and Renal Function

Plasma renin activity increased from 2.9-3.2 to 5-5.6 ng·ml$^{-1}$·h$^{-1}$ during hypoxia in both acetazolamide protocols, but did not change in controls, or with benzolamide and ethoxzolamide. Endothelin-1 plasma concentrations were about 0.4-0.57 pg/ml during normoxia, and increased to a maximum of 1.5±0.2 during hypoxia (p<0.05), there were no differences between the protocols.

Plasma sodium concentration varied between 139 and 143 mmol/l in all protocols and did not change during the experiments. Plasma potassium concentration was lower in all protocols in which CA inhibitors were applied (p<0.05) (Table 3, above).

In controls, urine output, sodium, and potassium excretion did not change after two hours of hypoxia. In all protocols in which CA inhibitors were applied, urine output, sodium, and potassium excretion were greater compared to controls during normoxia as well as during hypoxia (p<0.05) (Table 5). Glomerular filtration rates were significantly lower with all CA inhibitors, with the exception of iv AZ where there was a non-significant 12% reduction. The lower GFR with drug treatment was sustained throughout the hypoxic exposure (Table 5).

TABLE 5

Table 5. Renal excretion parameters in Controls, with iv AZ, po AZ, benzolamide, and ethoxzolamide during normoxia and hypoxia.

| | Normoxia 1$^{st}$ h | Hypoxia 2$^{nd}$ h | Hypoxia 3$^{rd}$ h |
|---|---|---|---|
| UV, µl · min$^{-1}$ · kg$^{-1}$ | | | |
| Controls | 27 ± 6 | 56 ± 16 | 24 ± 6 |
| iv AZ | 99 ± 13† | 161 ± 22† | 71 ± 10† |
| po AZ | 57 ± 11† | 83 ± 24 | 48 ± 11 |
| Benzolamide | 66 ± 7† | 104 ± 23 | 65 ± 15 |
| Ethoxzolamide | 52 ± 9† | 72 ± 22 | 45 ± 6 |
| U$_{Na}$V, µmol · min$^{-1}$ · kg$^{-1}$ | | | |
| Controls | 0.5 ± 0.1 | 0.3 ± 0.1 | 0.3 ± 0.1 |
| iv AZ | 3.9 ± 0.6† | 4.1 ± 0.6† | 4.1 ± 0.7† |
| po AZ | 1.8 ± 0.5 | 1.6 ± 0.3 | 1.3 ± 0.1 |
| Benzolamide | 4.0 ± 0.8† | 3.6 ± 0.6† | 3.3 ± 0.5† |
| Ethoxzolamide | 2.8 ± 0.5 | 3.6 ± 0.4† | 4.1 ± 0.5† |
| U$_K$V, µmol · min$^{-1}$ · kg$^{-1}$ | | | |
| Controls | 0.4 ± 0.1 | 0.4 ± 0.1 | 0.3 ± 0.1 |
| iv AZ | 3.5 ± 0.5† | 3.3 ± 0.5† | 3.2 ± 0.5† |
| po AZ | 1.6 ± 0.2† | 1.6 ± 0.3 | 1.6 ± 0.4 |
| Benzolamide | 4.0 ± 0.6† | 3.2 ± 0.6† | 3.4 ± 0.7† |
| Ethoxzolamide | 2.9 ± 0.1† | 3.3 ± 0.4† | 3.5 ± 0.4† |
| GFR, ml · min$^{-1}$ · kg$^{-1}$ | | | |
| Controls | 3.9 ± 0.2 | 4.0 ± 0.1 | 3.7 ± 0.1 |
| iv AZ | 3.4 ± 0.1 | 3.3 ± 0.1 | 3.4 ± 0.2 |
| po AZ | 3.1 ± 0.2† | 3.4 ± 0.3 | 3.3 ± 0.2 |
| Benzolamide | 2.9 ± 0.2† | 3.0 ± 0.2† | 3.2 ± 0.2† |
| Ethoxzolamide | 3.2 ± 0.2 | 3.1 ± 0.2† | 3.2 ± 0.2† |

UV, urine volume; U$_{Na}$V, urinary sodium concentration; U$_K$V, urinary potassium concentration; GFR, glomerular filtration rate. Values measured during one hour of normoxia and two hours of hypoxia. Means ± SEM, n = 6;
*p < 0.05 vs. normoxia,
†p < 0.05 vs. Controls.

Example 18

Acetazolamide Plasma Concentration

Representative acetazolamide plasma concentrations were measured in two individual dogs with iv and po AZ. During normoxia, acetazolamide plasma concentrations were comparable in both protocols (4.65±0.7 µg/ml po AZ vs. 5.3±0.6 µg/ml iv AZ). During hypoxia, acetazolamide concentrations remained stable with po AZ (4.35±0.75 µg/ml), whereas they increased with iv AZ (7.4±0.2 µg/ml) as consequence of the maintenance infusion.

The principle findings of this study are that acetazolamide inhibits HPV with a dose response relationship yielding reduction of HPV in concentrations and dosing relevant to humans taking conventional and tolerable doses (2-5 mg/kg). Furthermore, for the first time it is shown in live animals that acetazolamide does not inhibit HPV by carbonic anhydrase inhibition, since two other potent CA inhibitors are ineffective against HPV.

Example 19

Hypoxic Pulmonary Vasoconstriction (HPV)

In control dogs, mean pulmonary artery pressure and pulmonary vascular resistance increased with hypoxia (FIG. 10). This is consistent with earlier results and many studies in humans and animals, See Höhne C., et al., *J Appl Physiol* 97:515-521 (2004); Höhne C., et al., *J Appl Physiol* 90:1842-1848 (2001); Aaronson P. I., et al., *J Physiol* 570:53-58 (2006); and Hillier S. C., et al., *J Appl Physiol* 82:1084-1090 (1997), which are hereby incorporated by reference in their entirety. The stimulus for HPV is the decrease in oxygen tension of the pulmonary artery smooth muscle cells—and to a smaller extent, venular vascular smooth muscle cells—determined by O$_2$ tensions primarily in the alveolar gas. It has been shown that hypoxia leads to a rise in the intracellular calcium concentration [Ca$^{2+}$]$_i$ in pulmonary artery smooth muscle cells via several pathways that initiate and sustain smooth muscle contraction. See Aaronson P. I., et al., *J Physiol* 570:53-58 (2006), which is hereby incorporated by reference in its entirety.

In conscious dogs, iv acetazolamide applied at full CA-inhibiting concentrations (10 mg·kg$^{-1}$·h$^{-1}$) totally abolished HPV. See Höhne C., et al., *J Appl Physiol* 97:515-521 (2004), which is hereby incorporated by reference in its entirety. Applying an 80% lower dose (2 mg·kg$^{-1}$·h$^{-1}$) the increase in MPAP and PVR during acute hypoxia was still inhibited (FIGS. 10 and 11, Table 3, above). The values for arterial pH before and during hypoxia were not as low as those found with the high dose iv AZ (see Höhne C., et al., *J Appl Physiol* 97:515-521 (2004), which is hereby incorporated by reference in its entirety), supporting the known dose response relationship of acetazolamide on acid-base status in the dog. The effects of acetazolamide on HPV in live dogs are in line with results in rat pulmonary artery smooth muscle cells obtained by Shimoda et al. See Shimoda L. A., et al., [abstract] *Am J Respir Crit Care Med A*173, (2006), which is hereby incorporated by reference in its entirety. They demonstrated the functional presence of CA in these cells in the regulation of basal pH$_i$ under normal conditions. During hypoxia [Ca$^{2+}$]$_i$ increases, and acetazolamide inhibits this rise, by a mechanism(s) other than changes in the membrane potential (E$_m$) or blockade of voltage-sensitive membrane L-type calcium channels. Inhibition of the increase in [Ca$^{2+}$]$_i$ by acetazolamide in the pulmonary arterial vasculature may well explain the lack of HPV in acetazolamide-treated dogs.

To determine if intra- and/or extracellular CA inhibition is involved in the suppression of HPV by CA inhibitors benzolamide, a powerful, hydrophilic, non-permeant CA inhibitor, was used to inhibit only extracellular CA. Benzolamide did not inhibit the increase in mean pulmonary arterial pressure and pulmonary vascular resistance during hypoxia (FIG. 10, Table 4, above). This left intracellular CA as a possible target. To test if intracellular CA inhibition was involved in HPV inhibition ethoxzolamide, a cell membrane-permeant CA inhibitor was used. Similar to benzolamide, ethoxzolamide did not prevent the increase of MPAP and PVR during hypoxia (FIG. 10, Table 4, above). These findings in the live animal mirror the results of Shimoda et al. obtained in isolated pulmonary artery smooth muscle cells, showing that benzolamide and ethoxzolamide do not prevent the hypoxia related increase in $[Ca^{2+}]_i$. See Shimoda L. A., et al., [abstract] *Am J Respir Crit Care Med* A173, (2006) which is hereby incorporated by reference in its entirety. Despite the failure to prevent HPV, benzolamide and ethoxzolamide clearly exhibited potent CA inhibiting properties, reflected by the lower plasma bicarbonate concentrations and base excess during the normoxia and hypoxia period (Tables 3 and 4, above), increased urinary sodium and potassium excretion and reduction in GFR compared to controls (Table 5, above) These all are well known effects of CA inhibitors caused by renal bicarbonate excretion and by tissue $CO_2$ retention and indicate the efficacy of both drugs, as far as CA inhibition is concerned. See Swenson E. R., et al., *Eur Respir J* 12:1242-1247 (1998); Höhne C., et al., *J Appl Physiol* 97:515-521 (2004); Maren T. H., *Am J Physiol* 232:F291-297 (1977); and Swenson E. R., In: Chegwidden W R, Carter N D, Edwards Y H, editors. The Carbonic Anhydrases: New Horizon, $1^{st}$ ed. Oxford: Birkhauser Press; p. 281-341 (2000), which are hereby incorporated by reference in their entirety.

The effect of 5 mg/kg po AZ, given twice, 12 hours and one hour before the hypoxia exposure was tested. The time points and dosage were chosen to reflect the use of acetazolamide by mountaineers or those traveling to high altitude for AMS prevention. The effect on HPV as measured by MPAP was less pronounced compared to iv AZ, but it nevertheless had an almost equal effect on PVR during hypoxia (FIG. 10, Table 4, above). The lesser effect of po AZ on HPV and MPAP is likely due to the lower plasma concentrations during hypoxia compared with iv AZ (4.35±0.75 vs. 7.4±0.2 µg/ml) and to a slightly higher cardiac output. In addition, these dogs had greater metabolic acidosis (Table 5, above) due to a longer time of action of the drug on the kidney and more cumulative urinary bicarbonate loss. Metabolic acidosis is known to augment HPV and this may have also acted to blunt the effectiveness of the drug. See Lejeune P., et al., *Anesthesiol.* 73:256-64 (1990), which is hereby incorporated by reference in its entirety.

Example 20

Systemic Circulation, and Ventilatory Response

The systemic hemodynamic parameters of heart rate, mean arterial pressure, cardiac output, and systemic vascular resistance were similar in all protocols during the normoxia period (Table 4, above). The increases in heart rate and MAP during hypoxia in controls and during CA inhibition are comparable to former studies. See Höhne C., et al., *J Appl Physiol* 97:515-521 (2004) and Hohne C., et al., *J Appl Physiol* 90:1842-1848 (2001), which are hereby incorporated by reference in their entirety. Cardiac output, SVR and central venous pressure did not change in any of the protocols (Table 4, above), indicating that in the time frame of the study, CA inhibition caused no significant volume depletion, even when acetazolamide was given orally 12 hours before the experiment.

In controls, acute hypoxia increased minute ventilation by 35%, inducing a significant respiratory alkalosis (Tables 2 and 3, above). In normoxia, acetazolamide (both po and iv) and ethoxzolamide increased ventilation as reflected in lower $P_aCO_2$ values and increased minute ventilation. Benzolamide, however, did not appear to increase ventilation. With all CA inhibitors, there was increased ventilation with hypoxia, but the increase was least with benzolamide, reflecting the inability of benzolamide to penetrate to intracellular sites of CA. See Swenson E. R. et al., *J Appl Physiol* 73:230-237 (1993), which is hereby incorporated by reference in its entirety. The increase in minute ventilation in the present acetazolamide protocols (partial CA inhibition) was less pronounced than in the former study in which a fully inhibitory dose of acetazolamide was administered. See Hohne C., et al., *J Appl Physiol* 97:515-521 (2004), which is hereby incorporated by reference in its entirety.

Example 21

Renal and Acid-Base Effects

In all protocols with CA inhibition, urine volume, sodium and potassium excretion was greater than in controls during normoxia as well as during hypoxia (Table 5, above). This is caused by renal CA inhibition, increasing urinary excretion of the anion bicarbonate which for reasons of electroneutrality must be coupled with an increased excretion of the cations sodium and potassium. See Höhne C., et al., *J Appl Physiol* 97:515-521 (2004), which is hereby incorporated by reference in its entirety. The somewhat lower excretion rates for sodium and potassium during po AZ may be due to the lower dose of acetazolamide (lower plasma concentrations), but may also reflect counter-regulatory processes engaged to protect the body's sodium and potassium stores over the 12 hours following the first dose.

In summary, it was found that acetazolamide reduces hypoxic pulmonary vasoconstriction in a dose dependent-manner and is effective at dosing relevant to human use. The efficacy of acetazolamide as a HPV inhibitor does not appear to be related to CA inhibition, since neither intracellular enzyme inhibition by ethoxzolamide nor extracellular enzyme inhibition by benzolamide had an effect on HPV in the conscious dogs. With recent evidence in abstract form by Balonos et al. (see Balanos G. M., et al., Abstract presented at Experimental Biology, San Francisco: LB138, (April 2006), which is hereby incorporated by reference in its entirety) that acetazolamide (250 mg tid) reduces HPV by 50% in humans; there are solid grounds for a clinical trial of acetazolamide in HAPE prevention. Further studies should address whether a molecule lacking CA inhibitory activity and thus devoid of the unwanted systemic acid-base effects, but otherwise possessing equivalent molecular characteristics to acetazolamide, will have the same effect on HPV and perhaps on other forms of pulmonary hypertension.

Example 22

Effect of Inhalation Acetatolamide

This study was performed to determine whether acetazolamide given by inhalation to the lungs of unanesthetized dogs could reduce the rise in pulmonary artery pressure and pulmonary vascular resistance with exposure to breathing 12% oxygen for two hours. The data in Table 6 show that inhaled acetazolamide was successful in reducing the pulmonary vascular response to hypoxia and that the effect was comparable to that observed with acetazolamide given intravenously or by oral administration.

TABLE 6

| | Normoxia 1st h | Hypoxia 2nd h | Hypoxia 3rd h |
|---|---|---|---|
| $Pa_{O2}$, Torr | | | |
| Controls | 93 ± 1 | 36 ± 1* | 36 ± 1* |
| iv ACZ | 107 ± 3† | 37 ± 1* | 38 ± 1* |
| oral ACZ | 108 ± 2† | 37 ± 1* | 37 ± 1* |
| inhaled ACZ | 101 ± 2 | 39 ± 1* | 36 ± 1* |
| $Pa_{CO2}$, Torr | | | |
| Controls | 37 ± 1 | 29 ± 1* | 28 ± 1* |
| iv ACZ | 34 ± 1 | 30 ± 1 | 27 ± 1* |
| oral ACZ | 32 ± 1† | 28 ± 1* | 26 ± 1* |
| inhaled ACZ | 36 ± 1 | 26 ± 1* | 25 ± 1* |
| $V_E$, l/min | | | |
| Controls | 3.6 ± 0.4 | 5.5 ± 0.5 | 5.5 ± 0.5 |
| iv ACZ | 4.1 ± 0.4 | 6.5 ± 0.5* | 6.9 ± 0.5* |
| oral ACZ | 4.6 ± 0.3 | 6.6 ± 0.4* | 6.3 ± 0.2* |
| inhaled ACZ | 3.2 ± 0.2 | 5.5 ± 0.5* | 5.7 ± 0.4* |
| $ph_a$ | | | |
| Controls | 7.38 ± 0.01 | 7.45 ± 0.01* | 7.46 ± 0.01* |
| iv ACZ | 7.38 ± 0.01 | 7.41 ± 0.01 | 7.40 ± 0.01† |
| oral ACZ | 7.35 ± 0.01 | 7.40 ± 0.01*† | 7.42 ± 0.01*† |
| inhaled ACZ | 7.37 ± 0.01 | 7.43 ± 0.01* | 7.44 ± 0.01* |
| $HCO_{3a}$, mM | | | |
| Controls | 21.6 ± 0.6 | 20.0 ± 0.7 | 19.4 ± 0.5 |
| iv ACZ | 20.2 ± 0.4 | 18.5 ± 0.5 | 17.1 ± 0.5* |
| oral ACZ | 17.6 ± 0.3† | 16.7 ± 0.6† | 16.1 ± 0.4† |
| inhaled ACZ | 20.2 ± 0.5 | 17.1 ± 0.6*† | 16.4 ± 0.5*† |
| $BE_a$, mM | | | |
| Controls | −2.5 ± 0.6 | −2.3 ± 0.7 | −2.2 ± 1.0 |
| iv ACZ | −4.0 ± 0.5 | −4.6 ± 0.4 | −6.1 ± 0.6† |
| oral ACZ | −6.5 ± 0.3† | −6.3 ± 0.6† | −6.4 ± 0.4† |
| inhaled ACZ | −3.9 ± 0.6 | −5.2 ± 0.6† | −5.7 ± 0.7†* |
| HR, beats/min | | | |
| Controls | 79 ± 4 | 108 ± 8 | 103 ± 7 |
| iv ACZ | 74 ± 4 | 103 ± 6 | 106 ± 7 |
| oral ACZ | 85 ± 3 | 109 ± 5 | 102 ± 7 |
| inhaled ACZ | 85 ± 5 | 86 ± 6 | 100 ± 8 |
| MAP, mmHg | | | |
| Controls | 98 ± 4 | 108 ± 4 | 106 ± 8 |
| iv ACZ | 95 ± 5 | 102 ± 8 | 103 ± 7 |
| oral ACZ | 95 ± 3 | 106 ± 6 | 107 ± 6 |
| inhaled ACZ | 92 ± 4 | 105 ± 5 | 105 ± 5 |
| CO, l/min | | | |
| Controls | 2.6 ± 0.2 | 3.0 ± 0.2 | 2.7 ± 0.2 |
| iv ACZ | 2.6 ± 0.2 | 3.0 ± 0.4 | 2.9 ± 0.5 |
| oral ACZ | 2.3 ± 0.2 | 2.7 ± 0.2 | 2.3 ± 0.1 |
| inhaled ACZ | 2.5 ± 0.1 | 2.3 ± 0.2 | 2.5 ± 0.1 |
| SVR, dyn s$^{-1}$ cm | | | |
| Controls | 3006 ± 242 | 2983 ± 224 | 3086 ± 264 |
| iv ACZ | 2868 ± 331 | 2826 ± 382 | 3174 ± 422 |
| oral ACZ | 3361 ± 311 | 3200 ± 286 | 3670 ± 284 |
| inhaled ACZ | 2923 ± 174 | 3664 ± 321 | 3325 ± 202 |
| CVP, cmH$_2$O | | | |
| Controls | 2.1 ± 0.4 | 2.3 ± 0.4 | 1.8 ± 0.4 |
| in ACZ | 1.8 ± 0.3 | 2.2 ± 0.3 | 2.3 ± 0.4 |
| oral ACZ | 2.3 ± 0.3 | 1.9 ± 0.2 | 1.9 ± 0.2 |
| inhaled ACZ | 2.8 ± 0.3 | 2.5 ± 0.3 | 2.1 ± 0.2 |
| MPAP, mmHg | | | |
| Controls | 13 ± 1 | 19 ± 1* | 20 ± 1* |
| iv ACZ | 13 ± 1 | 15 ± 1† | 14 ± 1† |
| oral ACZ | 12 ± 1 | 17 ± 1* | 17 ± 1* |
| inhaled ACZ | 13 ± 1 | 15 ± 1† | 15 ± 1† |
| PVR, dyn s$^{-1}$ cm | | | |
| Controls | 269 ± 18 | 447 ± 39* | 473 ± 33* |
| iv ACZ | 283 ± 37 | 312 ± 36 | 305 ± 26† |
| oral ACZ | 298 ± 27 | 375 ± 33 | 431 ± 45* |
| inhaled ACZ | 298 ± 21 | 395 ± 29 | 388 ± 30 |
| PCWP, cmH$_2$O | | | |
| Controls | 4.1 ± 0.2 | 3.1 ± 0.1 | 3.9 ± 0.2 |
| iv ACZ | 3.8 ± 0.5 | 3.5 ± 0.3 | 3.7 ± 0.3 |
| oral ACZ | 3.9 ± 0.3 | 3.5 ± 0.3 | 3.5 ± 0.3 |
| inhaled ACZ | 4.3 ± 0.4 | 3.9 ± 0.4 | 3.6 ± 0.2 |
| UV, μ min$^{-1}$ kg$^{-1}$ | | | |
| Controls | 35 ± 8 | 48 ± 12 | 31 ± 6 |
| iv ACZ | 102 ± 12† | 135 ± 27† | 68 ± 12 |
| oral ACZ | 50 ± 9 | 84 ± 15 | 55 ± 8 |
| inhaled ACZ | 33 ± 8 | 99 ± 16*† | 81 ± 15† |
| $U_{Na}V$, μmol min | | | |
| Controls | 0.3 ± 0.1 | 0.4 ± 0.2 | 1.2 ± 0.9 |
| iv ACZ | 3.8 ± 0.6† | 4.0 ± 0.6† | 5.4 ± 1.2† |
| oral ACZ | 1.4 ± 0.6 | 1.7 ± 0.5 | 1.5 ± 0.4 |
| inhaled ACZ | 0.4 ± 0.1 | 8.0 ± 1.3† | 5.1 ± 0.7*† |
| $U_K V$, pmol min | | | |
| Controls | 0.3 ± 0.1 | 0.4 ± 0.1 | 1.1 ± 0.7 |
| iv ACZ | 4.8 ± 1.4† | 4.7 ± 1.1† | 5.3 ± 1.6† |
| oral ACZ | 1.7 ± 0.3 | 2.0 ± 0.4 | 1.9 ± 0.4 |
| inhaled ACZ | 0.5 ± 0.1 | 7.1 ± 0.7† | 4.8 ± 0.6† |
| GFR, ml min | | | |
| Controls | 4.0 ± 0.2 | 3.9 ± 0.1 | 3.9 ± 0.2 |
| iv ACZ | 3.5 ± 0.3 | 3.4 ± 0.3 | 3.8 ± 0.3 |
| oral ACZ | 3.0 ± 0.2† | 3.3 ± 0.2 | 3.3 ± 0.2 |
| inhaled ACZ | 4.0 ± 0.4 | 3.7 ± 0.3 | 3.6 ± 0.3 | iv ACZ: 2 mg/kg bodyweight bolus, followed by 2 mg/kg body weight per hour continuously (n = 6)
oral ACZ: 5 mg/kg bodyweight - 12 h, followed by 5 mg/kg bodyweight - 1 h (n = 8)
inhaled ACZ: 750 mg inhaled after 1 h of normoxia, followed by 2 h hypoxia (n − 8)

The data also show that some acetazolamide is absorbed by the airways into the blood stream. This is evidenced by the increase in urinary sodium excretion (an action of the drug on the kidney that only requires very low blood levels), but without sufficient blood levels to alter ventilation, an action requiring high blood levels. Thus, a potent effect on pulmonary artery pressure was achieved with only minimal effect elsewhere in the body.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of treating a subject for a pulmonary disease selected from the group consisting of hypoxic pulmonary vasoconstriction, pulmonary edema, pulmonary hypertension, asthma, chronic obstructive pulmonary disease, cystic fibrosis, interstitial fibrosis, high altitude residence, sleep apnea syndrome, and atrial septal defects, said method comprising:

administering to the subject a compound of the formula:

where $R_1$ and $R_3$ are each methyl and $R_2$ is hydrogen;

wherein the compound is administered orally, parenterally, subcutaneously, intravenously, intramuscularly, intraperitoneally, by intranasal instillation, by inhalation, and/or by application to mucous membranes of the nose, throat, and/or bronchial tubes;

under conditions effective to treat the pulmonary disease in the subject.

2. The method of claim 1, wherein the subject is human.

* * * * *